United States Patent
Saadat et al.

(10) Patent No.: US 11,882,996 B2
(45) Date of Patent: Jan. 30, 2024

(54) IN-VIVO VISUALIZATION SYSTEMS

(71) Applicant: Intuitive Surgical Operations, Inc., Sunnyvale, CA (US)

(72) Inventors: Vahid Saadat, Atherton, CA (US); Antony Jonathan Fields, San Francisco, CA (US); Zachary J. Malchano, San Francisco, CA (US); Chris Rothe, San Mateo, CA (US); Veerappan Swaminathan, Sunnyvale, CA (US); Jason Paul Watson, San Jose, CA (US); Bryan Wylie, San Jose, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 1112 days.

(21) Appl. No.: 16/567,066

(22) Filed: Sep. 11, 2019

(65) Prior Publication Data
US 2020/0000319 A1 Jan. 2, 2020

Related U.S. Application Data

(60) Division of application No. 14/714,992, filed on May 18, 2015, now Pat. No. 10,470,643, which is a
(Continued)

(51) Int. Cl.
*A61B 1/00* (2006.01)
*A61B 1/005* (2006.01)
(Continued)

(52) U.S. Cl.
CPC ........ *A61B 1/00085* (2013.01); *A61B 1/0052* (2013.01); *A61B 1/0055* (2013.01);
(Continued)

(58) Field of Classification Search
CPC . A61B 1/00085; A61B 1/0052; A61B 1/0055; A61B 1/3137; A61B 1/00089; A61B 1/015; A61B 1/05
See application file for complete search history.

(56) References Cited

U.S. PATENT DOCUMENTS 623,002 A 4/1899 Fitzgerald
623,022 A 4/1899 Johnson
(Continued)

FOREIGN PATENT DOCUMENTS

DE 2853466 A1 6/1979
DE 10028155 A1 12/2000
(Continued)

OTHER PUBLICATIONS

Tse HF., et al., "angiogenesis is Ischaemic Myccardium by Intramyocardial Autologous Bone Marrow Mononuclear Cell Implantation," Lancet, 2003, vol. 361, pp. 47-49.
(Continued)

*Primary Examiner* — Baisakhi Roy
(74) *Attorney, Agent, or Firm* — Haynes & Boone, LLP.

(57) ABSTRACT

A computer implemented method comprises receiving a model of a tissue region, steering a distal end of a catheter within a body to a first area of a tissue region, and obtaining a first image from the distal end of the catheter of the first area of the tissue region. The method further comprises mapping the first image of the first area of the tissue region to the model of the tissue region and displaying the first image of the first area of the tissue region on the model of the tissue region.

20 Claims, 19 Drawing Sheets

Related U.S. Application Data continuation of application No. 12/778,878, filed on May 12, 2010, now Pat. No. 9,055,906, which is a continuation-in-part of application No. 11/763,399, filed on Jun. 14, 2007, now Pat. No. 10,064,540.

(60) Provisional application No. 61/177,618, filed on May 12, 2009, provisional application No. 60/888,242, filed on Feb. 5, 2007, provisional application No. 60/871,415, filed on Dec. 21, 2006, provisional application No. 60/871,424, filed on Dec. 21, 2006, provisional application No. 60/806,926, filed on Jul. 10, 2006, provisional application No. 60/806,924, filed on Jul. 10, 2006, provisional application No. 60/804,801, filed on Jun. 14, 2006.

(51) Int. Cl.
*A61B 1/05* (2006.01)
*A61B 1/313* (2006.01)
*A61B 1/015* (2006.01)
*A61B 1/12* (2006.01)
*A61B 18/14* (2006.01)
*A61B 17/00* (2006.01)
*A61B 34/30* (2016.01)

(52) U.S. Cl.
CPC .......... *A61B 1/00089* (2013.01); *A61B 1/015* (2013.01); *A61B 1/05* (2013.01); *A61B 1/3137* (2013.01); *A61B 1/12* (2013.01); *A61B 18/1492* (2013.01); *A61B 2017/00314* (2013.01); *A61B 2034/306* (2016.02); *A61B 2218/002* (2013.01)

(56) References Cited

U.S. PATENT DOCUMENTS

| | | |
|---|---|---|
| 2,305,462 A | 12/1942 | Wolf |
| 2,453,862 A | 11/1948 | Salisbury |
| 3,559,651 A | 2/1971 | Moss |
| 3,831,587 A | 8/1974 | Boyd |
| 3,874,388 A | 4/1975 | King et al. |
| 3,903,877 A | 9/1975 | Terada |
| 4,175,545 A | 11/1979 | Termanini |
| 4,198,981 A | 4/1980 | Sinnreich |
| 4,326,529 A | 4/1982 | Doss et al. |
| 4,403,612 A | 9/1983 | Fogarty |
| 4,445,892 A | 5/1984 | Hussein et al. |
| 4,470,407 A | 9/1984 | Hussein |
| 4,517,976 A | 5/1985 | Murakoshi et al. |
| 4,569,335 A | 2/1986 | Tsuno |
| 4,576,146 A | 3/1986 | Kawazoe et al. |
| 4,615,333 A | 10/1986 | Taguchi |
| 4,619,247 A | 10/1986 | Inoue et al. |
| 4,676,258 A | 6/1987 | Inokuchi et al. |
| 4,681,093 A | 7/1987 | Ono et al. |
| 4,696,668 A | 9/1987 | Wilcox |
| 4,709,698 A | 12/1987 | Johnston et al. |
| 4,710,192 A | 12/1987 | Liotta et al. |
| 4,727,418 A | 2/1988 | Kato et al. |
| 4,772,260 A | 9/1988 | Heyden |
| 4,784,133 A | 11/1988 | Mackin |
| 4,838,246 A | 6/1989 | Hahn et al. |
| 4,848,323 A | 7/1989 | Marijnissen et al. |
| 4,880,015 A | 11/1989 | Nierman |
| 4,911,148 A | 3/1990 | Sosnowski et al. |
| 4,914,521 A | 4/1990 | Adair |
| 4,943,290 A | 7/1990 | Rexroth et al. |
| 4,950,285 A | 8/1990 | Wilk |
| 4,957,484 A | 9/1990 | Murtfeldt |
| 4,960,411 A | 10/1990 | Buchbinder |
| 4,961,738 A | 10/1990 | Mackin |
| 4,976,710 A | 12/1990 | Mackin |
| 4,991,578 A | 2/1991 | Cohen |
| 4,994,069 A | 2/1991 | Ritchart et al. |
| 4,998,916 A | 3/1991 | Hammerslag et al. |
| 4,998,972 A | 3/1991 | Chin et al. |
| 5,025,778 A | 6/1991 | Silverstein et al. |
| 5,047,028 A | 9/1991 | Qian |
| 5,057,106 A | 10/1991 | Kasevich et al. |
| 5,090,959 A | 2/1992 | Samson et al. |
| 5,123,428 A | 6/1992 | Schwarz |
| RE34,002 E | 7/1992 | Adair |
| 5,156,141 A | 10/1992 | Krebs et al. |
| 5,171,259 A | 12/1992 | Inoue |
| 5,197,457 A | 3/1993 | Adair |
| 5,270,810 A | 12/1993 | Nishimura |
| 5,281,238 A | 1/1994 | Chin et al. |
| 5,282,827 A | 2/1994 | Kensey et al. |
| 5,305,121 A | 4/1994 | Moll |
| 5,306,234 A | 4/1994 | Johnson |
| 5,313,934 A | 5/1994 | Wiita et al. |
| 5,313,943 A | 5/1994 | Houser et al. |
| 5,330,496 A | 7/1994 | Alferness |
| 5,334,159 A | 8/1994 | Turkel |
| 5,334,193 A | 8/1994 | Nardella |
| 5,336,252 A | 8/1994 | Cohen |
| 5,339,800 A | 8/1994 | Wiita et al. |
| 5,345,927 A | 9/1994 | Bonutti |
| 5,348,554 A | 9/1994 | Imran et al. |
| 5,353,792 A | 10/1994 | Luebbers et al. |
| 5,370,647 A | 12/1994 | Graber et al. |
| 5,373,840 A | 12/1994 | Knighton |
| 5,375,612 A | 12/1994 | Cottenceau et al. |
| 5,385,146 A | 1/1995 | Goldreyer |
| 5,385,148 A | 1/1995 | Lesh et al. |
| 5,391,182 A | 2/1995 | Chin |
| 5,391,199 A | 2/1995 | Ben-Haim |
| 5,403,311 A | 4/1995 | Abele et al. |
| 5,403,326 A | 4/1995 | Harrison et al. |
| 5,405,360 A | 4/1995 | Tovey |
| 5,405,376 A | 4/1995 | Mulier et al. |
| 5,409,483 A | 4/1995 | Campbell et al. |
| 5,411,016 A | 5/1995 | Kume et al. |
| 5,413,104 A | 5/1995 | Buijs et al. |
| 5,421,338 A | 6/1995 | Crowley et al. |
| 5,431,649 A | 7/1995 | Mulier et al. |
| 5,453,785 A | 9/1995 | Lenhardt et al. |
| 5,458,612 A | 10/1995 | Chin |
| 5,462,521 A | 10/1995 | Brucker et al. |
| 5,471,515 A | 11/1995 | Fossum et al. |
| 5,484,412 A | 1/1996 | Pierpont |
| 5,498,230 A | 3/1996 | Adair |
| 5,505,730 A | 4/1996 | Edwards |
| 5,515,853 A | 5/1996 | Smith et al. |
| 5,527,338 A | 6/1996 | Purdy |
| 5,549,603 A | 8/1996 | Feiring |
| 5,558,619 A | 9/1996 | Kami et al. |
| 5,571,088 A | 11/1996 | Lennox et al. |
| 5,575,756 A | 11/1996 | Karasawa et al. |
| 5,575,810 A | 11/1996 | Swanson et al. |
| 5,584,872 A | 12/1996 | Lafontaine et al. |
| 5,591,119 A | 1/1997 | Adair |
| 5,593,405 A | 1/1997 | Osypka |
| 5,593,422 A | 1/1997 | Muijs Van de Moer et al. |
| 5,593,424 A | 1/1997 | Northrup III |
| 5,643,282 A | 7/1997 | Kieturakis |
| 5,653,677 A | 8/1997 | Okada et al. |
| 5,662,671 A | 9/1997 | Barbut et al. |
| 5,665,062 A | 9/1997 | Houser |
| 5,672,153 A | 9/1997 | Lax et al. |
| 5,676,693 A | 10/1997 | Lafontaine |
| 5,681,308 A | 10/1997 | Edwards et al. |
| 5,695,448 A | 12/1997 | Kimura et al. |
| 5,697,281 A | 12/1997 | Eggers et al. |
| 5,697,882 A | 12/1997 | Eggers et al. |
| 5,709,224 A | 1/1998 | Behl et al. |
| 5,713,907 A | 2/1998 | Hogendijk et al. |
| 5,713,946 A | 2/1998 | Ben-Haim |
| 5,716,321 A | 2/1998 | Kerin et al. |
| 5,716,325 A | 2/1998 | Bonutti |
| 5,722,403 A | 3/1998 | McGee et al. |

(56) References Cited

U.S. PATENT DOCUMENTS

| | | |
|---|---|---|
| 5,725,523 A | 3/1998 | Mueller |
| 5,743,851 A | 4/1998 | Moll et al. |
| 5,746,747 A | 5/1998 | Mckeating |
| 5,749,846 A | 5/1998 | Edwards et al. |
| 5,749,889 A | 5/1998 | Bacich et al. |
| 5,749,890 A | 5/1998 | Shaknovich |
| 5,754,313 A | 5/1998 | Pelchy et al. |
| 5,766,137 A | 6/1998 | Omata |
| 5,769,846 A | 6/1998 | Edwards et al. |
| 5,792,045 A | 8/1998 | Adair |
| 5,797,903 A | 8/1998 | Swanson et al. |
| 5,823,947 A | 10/1998 | Yoon et al. |
| 5,827,175 A | 10/1998 | Tanaka |
| 5,827,268 A | 10/1998 | Laufer |
| 5,829,447 A | 11/1998 | Stevens et al. |
| 5,842,973 A | 12/1998 | Bullard |
| 5,843,118 A | 12/1998 | Sepetka et al. |
| 5,846,221 A | 12/1998 | Snoke et al. |
| 5,846,239 A | 12/1998 | Swanson et al. |
| 5,848,969 A | 12/1998 | Panescu et al. |
| 5,860,974 A | 1/1999 | Abele |
| 5,860,991 A | 1/1999 | Klein et al. |
| 5,865,791 A | 2/1999 | Whayne et al. |
| 5,873,815 A | 2/1999 | Kerin et al. |
| 5,879,366 A | 3/1999 | Shaw et al. |
| 5,895,417 A | 4/1999 | Pomeranz et al. |
| 5,897,487 A | 4/1999 | Ouchi |
| 5,897,553 A | 4/1999 | Mulier et al. |
| 5,902,328 A | 5/1999 | Lafontaine et al. |
| 5,904,651 A | 5/1999 | Swanson et al. |
| 5,908,445 A | 6/1999 | Whayne et al. |
| 5,916,147 A | 6/1999 | Boury |
| 5,925,038 A | 7/1999 | Panescu et al. |
| 5,928,250 A | 7/1999 | Koike et al. |
| 5,929,901 A | 7/1999 | Adair et al. |
| 5,937,614 A | 8/1999 | Watkins et al. |
| 5,941,845 A | 8/1999 | Tu et al. |
| 5,944,690 A | 8/1999 | Falwell et al. |
| 5,964,755 A | 10/1999 | Edwards |
| 5,968,053 A | 10/1999 | Revelas |
| 5,971,983 A | 10/1999 | Lesh |
| 5,980,484 A | 11/1999 | Ressemann et al. |
| 5,985,307 A | 11/1999 | Hanson et al. |
| 5,986,693 A | 11/1999 | Adair et al. |
| 5,997,571 A | 12/1999 | Farr et al. |
| 6,004,269 A | 12/1999 | Crowley et al. |
| 6,007,521 A | 12/1999 | Bidwell et al. |
| 6,012,457 A | 1/2000 | Lesh |
| 6,013,024 A | 1/2000 | Mitsuda et al. |
| 6,024,740 A | 2/2000 | Lesh et al. |
| 6,027,501 A | 2/2000 | Goble et al. |
| 6,036,685 A | 3/2000 | Mueller |
| 6,043,839 A | 3/2000 | Adair et al. |
| 6,047,218 A | 4/2000 | Whayne et al. |
| 6,063,077 A | 5/2000 | Schaer |
| 6,063,081 A | 5/2000 | Mulier et al. |
| 6,068,653 A | 5/2000 | Lafontaine |
| 6,071,279 A | 6/2000 | Whayne et al. |
| 6,071,302 A | 6/2000 | Sinofsky et al. |
| 6,081,740 A | 6/2000 | Gombrich et al. |
| 6,086,528 A | 7/2000 | Adair |
| 6,086,534 A | 7/2000 | Kesten |
| 6,099,498 A | 8/2000 | Addis |
| 6,099,514 A | 8/2000 | Sharkey et al. |
| 6,102,905 A | 8/2000 | Baxter et al. |
| 6,112,123 A | 8/2000 | Kelleher et al. |
| 6,115,626 A | 9/2000 | Whayne et al. |
| 6,123,703 A | 9/2000 | Tu et al. |
| 6,123,718 A | 9/2000 | Tu et al. |
| 6,129,724 A | 10/2000 | Fleischman et al. |
| 6,139,508 A | 10/2000 | Simpson et al. |
| 6,142,993 A | 11/2000 | Whayne et al. |
| 6,152,144 A | 11/2000 | Lesh et al. |
| 6,156,350 A | 12/2000 | Constantz |
| 6,159,203 A | 12/2000 | Sinofsky |
| 6,161,543 A | 12/2000 | Cox et al. |
| 6,164,283 A | 12/2000 | Lesh |
| 6,167,297 A | 12/2000 | Benaron |
| 6,168,591 B1 | 1/2001 | Sinofsky |
| 6,168,594 B1 | 1/2001 | Lafontaine et al. |
| 6,174,307 B1 | 1/2001 | Daniel et al. |
| 6,178,346 B1 | 1/2001 | Amundson et al. |
| 6,190,381 B1 | 2/2001 | Olsen et al. |
| 6,211,904 B1 | 4/2001 | Adair et al. |
| 6,224,553 B1 | 5/2001 | Nevo |
| 6,231,561 B1 | 5/2001 | Frazier et al. |
| 6,234,995 B1 | 5/2001 | Peacock, III |
| 6,235,044 B1 | 5/2001 | Root et al. |
| 6,237,605 B1 | 5/2001 | Vaska et al. |
| 6,238,393 B1 | 5/2001 | Mulier et al. |
| 6,240,312 B1 | 5/2001 | Alfano et al. |
| 6,254,598 B1 | 7/2001 | Edwards et al. |
| 6,258,083 B1 | 7/2001 | Daniel et al. |
| 6,261,226 B1 | 7/2001 | McKenna et al. |
| 6,263,224 B1 | 7/2001 | West |
| 6,266,551 B1 | 7/2001 | Osadchy et al. |
| 6,270,492 B1 | 8/2001 | Sinofsky |
| 6,275,255 B1 | 8/2001 | Adair et al. |
| 6,280,450 B1 | 8/2001 | McGuckin, Jr. |
| 6,290,689 B1 | 9/2001 | Delaney et al. |
| 6,306,081 B1 | 10/2001 | Ishikawa et al. |
| 6,310,642 B1 | 10/2001 | Adair et al. |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,315,777 B1 | 11/2001 | Comben |
| 6,315,778 B1 | 11/2001 | Gambale et al. |
| 6,322,536 B1 | 11/2001 | Rosengart et al. |
| 6,325,797 B1 | 12/2001 | Stewart et al. |
| 6,328,727 B1 | 12/2001 | Frazier et al. |
| 6,352,503 B1 | 3/2002 | Matsui et al. |
| 6,358,247 B1 | 3/2002 | Altman et al. |
| 6,358,248 B1 | 3/2002 | Mulier et al. |
| 6,375,654 B1 | 4/2002 | McIntyre |
| 6,379,345 B1 | 4/2002 | Constantz |
| 6,383,195 B1 | 5/2002 | Richard |
| 6,385,476 B1 | 5/2002 | Osadchy et al. |
| 6,387,043 B1 | 5/2002 | Yoon |
| 6,387,071 B1 | 5/2002 | Constantz |
| 6,394,096 B1 | 5/2002 | Constantz |
| 6,396,873 B1 | 5/2002 | Goldstein et al. |
| 6,398,780 B1 | 6/2002 | Farley et al. |
| 6,401,719 B1 | 6/2002 | Farley et al. |
| 6,409,722 B1 | 6/2002 | Hoey et al. |
| 6,416,511 B1 | 7/2002 | Lesh et al. |
| 6,419,669 B1 | 7/2002 | Frazier et al. |
| 6,423,051 B1 | 7/2002 | Kaplan et al. |
| 6,423,055 B1 | 7/2002 | Farr et al. |
| 6,423,058 B1 | 7/2002 | Edwards et al. |
| 6,428,536 B2 | 8/2002 | Panescu et al. |
| 6,436,118 B1 | 8/2002 | Kayan |
| 6,440,061 B1 | 8/2002 | Wenner et al. |
| 6,440,119 B1 | 8/2002 | Nakada et al. |
| 6,458,151 B1 | 10/2002 | Saltiel |
| 6,461,327 B1 | 10/2002 | Addis et al. |
| 6,464,697 B1 | 10/2002 | Edwards et al. |
| 6,474,340 B1 | 11/2002 | Vaska et al. |
| 6,475,223 B1 | 11/2002 | Werp et al. |
| 6,478,769 B1 | 11/2002 | Parker |
| 6,482,162 B1 | 11/2002 | Moore |
| 6,484,727 B1 | 11/2002 | Vaska et al. |
| 6,485,489 B2 | 11/2002 | Teirstein et al. |
| 6,488,671 B1 | 12/2002 | Constantz et al. |
| 6,494,902 B2 | 12/2002 | Hoey et al. |
| 6,497,651 B1 | 12/2002 | Kan et al. |
| 6,497,705 B2 | 12/2002 | Comben |
| 6,500,174 B1 | 12/2002 | Maguire et al. |
| 6,502,576 B1 | 1/2003 | Lesh |
| 6,514,249 B1 | 2/2003 | Maguire et al. |
| 6,517,533 B1 | 2/2003 | Swaminathan |
| 6,527,979 B2 | 3/2003 | Constantz et al. |
| 6,532,380 B1 | 3/2003 | Close et al. |
| 6,533,767 B2 | 3/2003 | Johansson et al. |
| 6,537,272 B2 | 3/2003 | Christopherson et al. |

(56) References Cited

U.S. PATENT DOCUMENTS

| | | |
|---|---|---|
| 6,538,375 B1 | 3/2003 | Duggal et al. |
| 6,540,733 B2 | 4/2003 | Constantz et al. |
| 6,540,744 B2 | 4/2003 | Hassett et al. |
| 6,544,195 B2 | 4/2003 | Wilson et al. |
| 6,547,780 B1 | 4/2003 | Sinofsky |
| 6,549,800 B1 | 4/2003 | Atalar et al. |
| 6,558,375 B1 | 5/2003 | Sinofsky et al. |
| 6,558,382 B2 | 5/2003 | Jahns et al. |
| 6,562,020 B1 | 5/2003 | Constantz et al. |
| 6,572,609 B1 | 6/2003 | Farr et al. |
| 6,579,285 B2 | 6/2003 | Sinofsky |
| 6,585,732 B2 | 7/2003 | Mulier et al. |
| 6,587,709 B2 | 7/2003 | Solf et al. |
| 6,593,884 B1 | 7/2003 | Gilboa et al. |
| 6,605,055 B1 | 8/2003 | Sinofsky et al. |
| 6,613,062 B1 | 9/2003 | Leckrone et al. |
| 6,622,732 B2 | 9/2003 | Constantz |
| 6,626,855 B1 | 9/2003 | Weng et al. |
| 6,626,899 B2 | 9/2003 | Houser et al. |
| 6,626,900 B1 | 9/2003 | Sinofsky et al. |
| 6,632,171 B2 | 10/2003 | Iddan et al. |
| 6,635,070 B2 | 10/2003 | Leeflang et al. |
| 6,645,202 B1 | 11/2003 | Pless et al. |
| 6,650,923 B1 | 11/2003 | Lesh et al. |
| 6,658,279 B2 | 12/2003 | Swanson et al. |
| 6,659,940 B2 | 12/2003 | Adler |
| 6,663,821 B2 | 12/2003 | Seward |
| 6,673,090 B2 | 1/2004 | Root et al. |
| 6,676,656 B2 | 1/2004 | Sinofsky |
| 6,679,836 B2 | 1/2004 | Couvillon, Jr. |
| 6,682,526 B1 | 1/2004 | Jones et al. |
| 6,689,051 B2 | 2/2004 | Nakada et al. |
| 6,689,128 B2 | 2/2004 | Sliwa et al. |
| 6,692,430 B2 | 2/2004 | Adler |
| 6,701,581 B2 | 3/2004 | Senovich et al. |
| 6,701,931 B2 | 3/2004 | Sliwa et al. |
| 6,702,780 B1 | 3/2004 | Gilboa et al. |
| 6,704,043 B2 | 3/2004 | Goldstein et al. |
| 6,706,039 B2 | 3/2004 | Mulier et al. |
| 6,712,798 B2 | 3/2004 | Constantz |
| 6,719,747 B2 | 4/2004 | Constantz et al. |
| 6,719,755 B2 | 4/2004 | Sliwa et al. |
| 6,730,063 B2 | 5/2004 | Delaney et al. |
| 6,736,810 B2 | 5/2004 | Hoey et al. |
| 6,749,617 B1 | 6/2004 | Palasis et al. |
| 6,751,492 B2 | 6/2004 | Ben-Haim |
| 6,755,790 B2 | 6/2004 | Stewart et al. |
| 6,755,811 B1 | 6/2004 | Constantz |
| 6,764,487 B2 | 7/2004 | Mulier et al. |
| 6,770,070 B1 | 8/2004 | Balbierz |
| 6,771,996 B2 | 8/2004 | Bowe et al. |
| 6,773,402 B2 | 8/2004 | Govari et al. |
| 6,780,151 B2 | 8/2004 | Grabover et al. |
| 6,805,128 B1 | 10/2004 | Pless et al. |
| 6,805,129 B1 | 10/2004 | Pless et al. |
| 6,811,562 B1 | 11/2004 | Pless |
| 6,833,814 B2 | 12/2004 | Gilboa et al. |
| 6,840,923 B1 | 1/2005 | Lapcevic |
| 6,840,936 B2 | 1/2005 | Sliwa et al. |
| 6,849,073 B2 | 2/2005 | Hoey et al. |
| 6,858,005 B2 | 2/2005 | Ohline et al. |
| 6,858,026 B2 | 2/2005 | Sliwa et al. |
| 6,858,905 B2 | 2/2005 | Hsu et al. |
| 6,863,668 B2 | 3/2005 | Gillespie et al. |
| 6,866,651 B2 | 3/2005 | Constantz |
| 6,887,237 B2 | 5/2005 | Mcgaffigan |
| 6,892,091 B1 | 5/2005 | Ben-Haim et al. |
| 6,896,690 B1 | 5/2005 | Lambrecht et al. |
| 6,899,672 B2 | 5/2005 | Chin et al. |
| 6,915,154 B1 | 7/2005 | Docherty et al. |
| 6,916,284 B2 | 7/2005 | Moriyama |
| 6,916,286 B2 | 7/2005 | Kazakevich |
| 6,923,805 B1 | 8/2005 | Lafontaine et al. |
| 6,929,010 B2 | 8/2005 | Vaska et al. |
| 6,932,809 B2 | 8/2005 | Sinofsky |
| 6,939,348 B2 | 9/2005 | Malecki et al. |
| 6,942,657 B2 | 9/2005 | Sinofsky et al. |
| 6,949,095 B2 | 9/2005 | Vaska et al. |
| 6,953,457 B2 | 10/2005 | Farr et al. |
| 6,955,173 B2 | 10/2005 | Lesh |
| 6,958,069 B2 | 10/2005 | Shipp et al. |
| 6,962,589 B2 | 11/2005 | Mulier et al. |
| 6,971,394 B2 | 12/2005 | Sliwa et al. |
| 6,974,464 B2 | 12/2005 | Quijano et al. |
| 6,979,290 B2 | 12/2005 | Mourlas et al. |
| 6,982,740 B2 | 1/2006 | Adair et al. |
| 6,984,232 B2 | 1/2006 | Vanney et al. |
| 6,994,094 B2 | 2/2006 | Schwartz |
| 7,001,329 B2 | 2/2006 | Kobayashi et al. |
| 7,019,610 B2 | 3/2006 | Creighton et al. |
| 7,025,746 B2 | 4/2006 | Tal |
| 7,030,904 B2 | 4/2006 | Adair et al. |
| 7,041,098 B2 | 5/2006 | Farley et al. |
| 7,042,487 B2 | 5/2006 | Nakashima |
| 7,044,135 B2 | 5/2006 | Lesh |
| 7,052,493 B2 | 5/2006 | Vaska et al. |
| 7,090,683 B2 | 8/2006 | Brock et al. |
| 7,118,566 B2 | 10/2006 | Jahns |
| 7,156,845 B2 | 1/2007 | Mulier et al. |
| 7,163,534 B2 | 1/2007 | Brucker et al. |
| 7,166,537 B2 | 1/2007 | Jacobsen et al. |
| 7,169,144 B2 | 1/2007 | Hoey et al. |
| 7,179,224 B2 | 2/2007 | Willis |
| 7,186,214 B2 | 3/2007 | Ness |
| 7,207,984 B2 | 4/2007 | Farr et al. |
| 7,217,268 B2 | 5/2007 | Eggers et al. |
| 7,242,832 B2 | 7/2007 | Carlin et al. |
| 7,247,155 B2 | 7/2007 | Hoey et al. |
| 7,261,711 B2 | 8/2007 | Mulier et al. |
| 7,263,397 B2 | 8/2007 | Hauck et al. |
| 7,276,061 B2 | 10/2007 | Schaer et al. |
| 7,309,328 B2 | 12/2007 | Kaplan et al. |
| 7,322,934 B2 | 1/2008 | Miyake et al. |
| 7,323,001 B2 | 1/2008 | Clubb et al. |
| 7,416,552 B2 | 8/2008 | Paul et al. |
| 7,435,248 B2 | 10/2008 | Taimisto et al. |
| 7,527,625 B2 | 5/2009 | Knight et al. |
| 7,534,204 B2 | 5/2009 | Starksen et al. |
| 7,534,294 B1 | 5/2009 | Gaynor et al. |
| 7,569,052 B2 | 8/2009 | Phan et al. |
| 7,569,952 B1 | 8/2009 | Bono et al. |
| 7,736,347 B2 | 6/2010 | Kaplan et al. |
| 7,758,499 B2 | 7/2010 | Adler |
| 7,860,555 B2 | 12/2010 | Saadat |
| 7,860,556 B2 | 12/2010 | Saadat |
| 7,918,787 B2 | 4/2011 | Saadat |
| 7,919,610 B2 | 4/2011 | Serebriiskii et al. |
| 7,930,016 B1 | 4/2011 | Saadat |
| 8,050,746 B2 | 11/2011 | Saadat et al. |
| 8,078,266 B2 | 12/2011 | Saadat et al. |
| 8,131,350 B2 | 3/2012 | Saadat et al. |
| 8,137,333 B2 | 3/2012 | Saadat et al. |
| 8,221,310 B2 | 7/2012 | Saadat et al. |
| 8,235,985 B2 | 8/2012 | Saadat et al. |
| 8,333,012 B2 | 12/2012 | Rothe et al. |
| 8,417,321 B2 | 4/2013 | Saadat et al. |
| 8,419,613 B2 | 4/2013 | Saadat et al. |
| 8,475,361 B2 | 7/2013 | Barlow et al. |
| 8,657,805 B2 | 2/2014 | Peh et al. |
| 8,758,229 B2 | 6/2014 | Saadat et al. |
| 8,814,845 B2 | 8/2014 | Saadat et al. |
| 8,906,007 B2 | 12/2014 | Bonn et al. |
| 8,934,962 B2 | 1/2015 | Saadat et al. |
| 9,055,906 B2 | 6/2015 | Saadat et al. |
| 9,155,587 B2 | 10/2015 | Willis et al. |
| 9,192,287 B2 | 11/2015 | Saadat et al. |
| 9,226,648 B2 | 1/2016 | Saadat et al. |
| 9,332,893 B2 | 5/2016 | Saadat et al. |
| 9,510,732 B2 | 12/2016 | Miller et al. |
| 9,526,401 B2 | 12/2016 | Saadat et al. |
| 10,004,388 B2 | 6/2018 | Saadat et al. |
| 10,064,540 B2 | 9/2018 | Saadat et al. |
| 10,070,772 B2 | 9/2018 | Peh et al. |
| 10,092,172 B2 | 10/2018 | Peh et al. |

(56) References Cited

U.S. PATENT DOCUMENTS

| | | | |
|---|---|---|---|
| 10,278,588 B2 | 5/2019 | Saadat et al. | |
| 10,368,729 B2 | 8/2019 | Miller et al. | |
| 10,390,685 B2 | 8/2019 | Saadat et al. | |
| 10,463,237 B2 | 11/2019 | Saadat et al. | |
| 10,470,643 B2 | 11/2019 | Saadat et al. | |
| 10,555,788 B2* | 2/2020 | Panescu | A61B 34/30 |
| 10,772,492 B2 | 9/2020 | Miller et al. | |
| 11,304,771 B2* | 4/2022 | Panescu | A61B 1/00055 |
| 11,337,594 B2 | 5/2022 | Saadat et al. | |
| 11,406,250 B2 | 8/2022 | Saadat et al. | |
| 11,478,152 B2 | 10/2022 | Saadat et al. | |
| 2001/0020126 A1 | 9/2001 | Swanson et al. | |
| 2001/0039416 A1 | 11/2001 | Moorman et al. | |
| 2001/0047136 A1 | 11/2001 | Domanik et al. | |
| 2001/0047184 A1 | 11/2001 | Connors | |
| 2001/0055413 A1* | 12/2001 | Florent | G06T 7/149 |
| | | | 600/407 |
| 2002/0004644 A1 | 1/2002 | Koblish | |
| 2002/0026145 A1 | 2/2002 | Bagaoisan et al. | |
| 2002/0035311 A1 | 3/2002 | Ouchi | |
| 2002/0054852 A1 | 5/2002 | Cate | |
| 2002/0065455 A1 | 5/2002 | Ben-Haim et al. | |
| 2002/0072710 A1 | 6/2002 | Stewart et al. | |
| 2002/0077594 A1 | 6/2002 | Chien et al. | |
| 2002/0077642 A1 | 6/2002 | Patel et al. | |
| 2002/0087169 A1 | 7/2002 | Brock et al. | |
| 2002/0091304 A1 | 7/2002 | Ogura et al. | |
| 2002/0138088 A1 | 9/2002 | Nash et al. | |
| 2002/0161377 A1 | 10/2002 | Rabkin | |
| 2002/0165598 A1 | 11/2002 | Wahr et al. | |
| 2002/0169377 A1 | 11/2002 | Khairkhahan et al. | |
| 2002/0173815 A1 | 11/2002 | Hogendijk et al. | |
| 2003/0009085 A1 | 1/2003 | Arai et al. | |
| 2003/0014010 A1 | 1/2003 | Carpenter et al. | |
| 2003/0018358 A1 | 1/2003 | Saadat | |
| 2003/0035156 A1 | 2/2003 | Cooper | |
| 2003/0036698 A1 | 2/2003 | Kohler et al. | |
| 2003/0065267 A1 | 4/2003 | Smith | |
| 2003/0069593 A1 | 4/2003 | Tremulis et al. | |
| 2003/0120142 A1 | 6/2003 | Dubuc et al. | |
| 2003/0123606 A1* | 7/2003 | Mollus | A61B 6/541 |
| | | | 378/42 |
| 2003/0130572 A1 | 7/2003 | Phan et al. | |
| 2003/0144657 A1 | 7/2003 | Bowe et al. | |
| 2003/0171741 A1 | 9/2003 | Ziebol et al. | |
| 2003/0181939 A1 | 9/2003 | Bonutti | |
| 2003/0208222 A1 | 11/2003 | Zadno-Azizi | |
| 2003/0212394 A1 | 11/2003 | Pearson et al. | |
| 2003/0220574 A1 | 11/2003 | Markus et al. | |
| 2003/0222325 A1 | 12/2003 | Jacobsen et al. | |
| 2003/0236493 A1 | 12/2003 | Mauch | |
| 2004/0044350 A1 | 3/2004 | Martin et al. | |
| 2004/0049211 A1 | 3/2004 | Tremulis et al. | |
| 2004/0054335 A1 | 3/2004 | Lesh et al. | |
| 2004/0054389 A1 | 3/2004 | Osypka | |
| 2004/0082833 A1 | 4/2004 | Adler et al. | |
| 2004/0097788 A1* | 5/2004 | Mourlas | A61B 1/05 |
| | | | 600/116 |
| 2004/0097792 A1 | 5/2004 | Moll et al. | |
| 2004/0097805 A1* | 5/2004 | Verard | A61B 8/4254 |
| | | | 600/428 |
| 2004/0098031 A1 | 5/2004 | Van Der Burg et al. | |
| 2004/0117032 A1 | 6/2004 | Roth | |
| 2004/0133113 A1 | 7/2004 | Krishnan | |
| 2004/0138529 A1 | 7/2004 | Wiltshire et al. | |
| 2004/0138707 A1 | 7/2004 | Greenhalgh | |
| 2004/0147806 A1 | 7/2004 | Adler | |
| 2004/0147911 A1 | 7/2004 | Sinofsky | |
| 2004/0147912 A1 | 7/2004 | Sinofsky | |
| 2004/0147913 A1 | 7/2004 | Sinofsky | |
| 2004/0158143 A1 | 8/2004 | Flaherty et al. | |
| 2004/0158289 A1 | 8/2004 | Girouard et al. | |
| 2004/0165766 A1 | 8/2004 | Goto | |
| 2004/0167503 A1 | 8/2004 | Sinofsky | |
| 2004/0181237 A1 | 9/2004 | Forde et al. | |
| 2004/0199052 A1 | 10/2004 | Banik et al. | |
| 2004/0210111 A1 | 10/2004 | Okada | |
| 2004/0210239 A1 | 10/2004 | Nash et al. | |
| 2004/0210278 A1 | 10/2004 | Boll et al. | |
| 2004/0215180 A1 | 10/2004 | Starkebaum et al. | |
| 2004/0220471 A1 | 11/2004 | Schwartz | |
| 2004/0230131 A1 | 11/2004 | Kassab et al. | |
| 2004/0248837 A1 | 12/2004 | Raz et al. | |
| 2004/0249367 A1 | 12/2004 | Saadat et al. | |
| 2004/0254523 A1 | 12/2004 | Fitzgerald et al. | |
| 2004/0260182 A1 | 12/2004 | Zuluaga et al. | |
| 2004/0267084 A1 | 12/2004 | Navia et al. | |
| 2005/0004597 A1 | 1/2005 | McGuckin et al. | |
| 2005/0014995 A1 | 1/2005 | Amundson et al. | |
| 2005/0015048 A1 | 1/2005 | Chiu et al. | |
| 2005/0020914 A1 | 1/2005 | Amundson et al. | |
| 2005/0027163 A1 | 2/2005 | Chin et al. | |
| 2005/0038419 A9 | 2/2005 | Arnold et al. | |
| 2005/0059862 A1 | 3/2005 | Phan | |
| 2005/0059954 A1 | 3/2005 | Constantz | |
| 2005/0059965 A1 | 3/2005 | Eberl et al. | |
| 2005/0059984 A1 | 3/2005 | Chanduszko et al. | |
| 2005/0065504 A1 | 3/2005 | Melsky et al. | |
| 2005/0080336 A1* | 4/2005 | Byrd | A61B 8/065 |
| | | | 600/509 |
| 2005/0090818 A1 | 4/2005 | Pike et al. | |
| 2005/0096502 A1 | 5/2005 | Khalili | |
| 2005/0096643 A1 | 5/2005 | Brucker et al. | |
| 2005/0101984 A1 | 5/2005 | Chanduszko et al. | |
| 2005/0107736 A1 | 5/2005 | Landman et al. | |
| 2005/0124969 A1 | 6/2005 | Fitzgerald et al. | |
| 2005/0131401 A1 | 6/2005 | Malecki et al. | |
| 2005/0154252 A1 | 7/2005 | Sharkey et al. | |
| 2005/0159702 A1 | 7/2005 | Sekiguchi et al. | |
| 2005/0165272 A1 | 7/2005 | Okada et al. | |
| 2005/0165279 A1 | 7/2005 | Adler et al. | |
| 2005/0165391 A1 | 7/2005 | Maguire et al. | |
| 2005/0165466 A1 | 7/2005 | Morris et al. | |
| 2005/0197530 A1 | 9/2005 | Wallace et al. | |
| 2005/0197623 A1* | 9/2005 | Leeflang | A61B 1/0055 |
| | | | 604/95.04 |
| 2005/0215895 A1 | 9/2005 | Popp et al. | |
| 2005/0222554 A1 | 10/2005 | Wallace et al. | |
| 2005/0222557 A1 | 10/2005 | Baxter et al. | |
| 2005/0222558 A1 | 10/2005 | Baxter et al. | |
| 2005/0228452 A1* | 10/2005 | Mourlas | A61M 25/1002 |
| | | | 606/41 |
| 2005/0234436 A1 | 10/2005 | Baxter et al. | |
| 2005/0234437 A1 | 10/2005 | Baxter et al. | |
| 2005/0267328 A1 | 12/2005 | Blumzvig et al. | |
| 2005/0288632 A1 | 12/2005 | Willard | |
| 2006/0009715 A1 | 1/2006 | Khairkhahan et al. | |
| 2006/0009737 A1 | 1/2006 | Whiting et al. | |
| 2006/0015096 A1 | 1/2006 | Hauck et al. | |
| 2006/0022234 A1 | 2/2006 | Adair et al. | |
| 2006/0025651 A1 | 2/2006 | Adler et al. | |
| 2006/0025787 A1 | 2/2006 | Morales et al. | |
| 2006/0058598 A1 | 3/2006 | Esposito | |
| 2006/0069303 A1 | 3/2006 | Couvillon | |
| 2006/0069313 A1 | 3/2006 | Couvillon, Jr. et al. | |
| 2006/0074398 A1 | 4/2006 | Whiting et al. | |
| 2006/0084839 A1 | 4/2006 | Mourlas et al. | |
| 2006/0084945 A1 | 4/2006 | Moll et al. | |
| 2006/0089637 A1 | 4/2006 | Werneth et al. | |
| 2006/0111614 A1 | 5/2006 | Saadat et al. | |
| 2006/0111692 A1 | 5/2006 | Hlavka et al. | |
| 2006/0122587 A1 | 6/2006 | Sharareh | |
| 2006/0146172 A1 | 7/2006 | Jacobsen et al. | |
| 2006/0149129 A1 | 7/2006 | Watts et al. | |
| 2006/0149331 A1 | 7/2006 | Mann et al. | |
| 2006/0155242 A1 | 7/2006 | Constantz | |
| 2006/0161133 A1 | 7/2006 | Laird et al. | |
| 2006/0167439 A1 | 7/2006 | Kalser et al. | |
| 2006/0183992 A1 | 8/2006 | Kawashima | |
| 2006/0195060 A1 | 8/2006 | Navia et al. | |
| 2006/0217755 A1 | 9/2006 | Eversull et al. | |
| 2006/0224167 A1 | 10/2006 | Weisenburgh et al. | |
| 2006/0253113 A1 | 11/2006 | Arnold et al. | |
| 2006/0258909 A1 | 11/2006 | Saadat et al. | |

(56) References Cited

U.S. PATENT DOCUMENTS

| | | |
|---|---|---|
| 2006/0271032 A1 | 11/2006 | Chin et al. |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1 | 2/2007 | Moll et al. |
| 2007/0043413 A1 | 2/2007 | Eversull et al. |
| 2007/0049923 A1 | 3/2007 | Jahns |
| 2007/0055142 A1 | 3/2007 | Webler |
| 2007/0078451 A1 | 4/2007 | Arnold et al. |
| 2007/0083099 A1 | 4/2007 | Henderson et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100324 A1 | 5/2007 | Tempel et al. |
| 2007/0106113 A1 | 5/2007 | Ravo |
| 2007/0106146 A1 | 5/2007 | Altmann et al. |
| 2007/0106214 A1 | 5/2007 | Gray et al. |
| 2007/0106287 A1 | 5/2007 | O'Sullivan |
| 2007/0135826 A1 | 6/2007 | Zaver et al. |
| 2007/0167801 A1 | 7/2007 | Webler et al. |
| 2007/0185404 A1* | 8/2007 | Hauck ............... A61B 34/30 606/41 |
| 2007/0185485 A1* | 8/2007 | Hauck ............... A61B 34/20 606/41 |
| 2007/0198008 A1* | 8/2007 | Hauck ............... A61B 5/6885 606/41 |
| 2007/0213584 A1 | 9/2007 | Kim et al. |
| 2007/0225558 A1* | 9/2007 | Hauck ............... A61B 5/6885 348/45 |
| 2007/0239010 A1 | 10/2007 | Johnson |
| 2007/0265609 A1 | 11/2007 | Thapliyal et al. |
| 2007/0265610 A1 | 11/2007 | Thapliyal et al. |
| 2007/0270639 A1 | 11/2007 | Long |
| 2007/0270686 A1 | 11/2007 | Ritter et al. |
| 2007/0282371 A1 | 12/2007 | Lee et al. |
| 2007/0299456 A1 | 12/2007 | Teague |
| 2008/0009747 A1 | 1/2008 | Saadat et al. |
| 2008/0009859 A1 | 1/2008 | Auth et al. |
| 2008/0015563 A1 | 1/2008 | Hoey et al. |
| 2008/0015569 A1 | 1/2008 | Saadat et al. |
| 2008/0027464 A1 | 1/2008 | Moll et al. |
| 2008/0033241 A1 | 2/2008 | Peh et al. |
| 2008/0057106 A1 | 3/2008 | Erickson et al. |
| 2008/0058590 A1 | 3/2008 | Saadat et al. |
| 2008/0058836 A1 | 3/2008 | Moll et al. |
| 2008/0097476 A1 | 4/2008 | Peh et al. |
| 2008/0183081 A1 | 7/2008 | Lys et al. |
| 2008/0214889 A1 | 9/2008 | Saadat et al. |
| 2008/0228032 A1 | 9/2008 | Starksen et al. |
| 2008/0234834 A1 | 9/2008 | Meade et al. |
| 2008/0275300 A1 | 11/2008 | Rothe et al. |
| 2008/0287790 A1 | 11/2008 | Li |
| 2008/0287803 A1* | 11/2008 | Li ............... A61B 8/5238 382/128 |
| 2008/0287805 A1 | 11/2008 | Li |
| 2008/0287961 A1 | 11/2008 | Miyamoto et al. |
| 2008/0319258 A1 | 12/2008 | Thompson |
| 2009/0030276 A1 | 1/2009 | Saadat et al. |
| 2009/0030412 A1 | 1/2009 | Willis et al. |
| 2009/0048480 A1 | 2/2009 | Klenk et al. |
| 2009/0054805 A1 | 2/2009 | Boyle, Jr. |
| 2009/0062790 A1 | 3/2009 | Malchano et al. |
| 2009/0062871 A1 | 3/2009 | Chin et al. |
| 2009/0076476 A1* | 3/2009 | Barbagli ............... A61B 5/1076 600/587 |
| 2009/0076489 A1 | 3/2009 | Welches et al. |
| 2009/0082623 A1 | 3/2009 | Rothe et al. |
| 2009/0125022 A1 | 5/2009 | Saadat et al. |
| 2009/0143640 A1 | 6/2009 | Saadat et al. |
| 2009/0187074 A1 | 7/2009 | Saadat et al. |
| 2009/0203962 A1 | 8/2009 | Miller et al. |
| 2009/0227999 A1 | 9/2009 | Willis et al. |
| 2009/0264727 A1 | 10/2009 | Markowitz et al. |
| 2009/0267773 A1 | 10/2009 | Markowitz et al. |
| 2009/0326572 A1 | 12/2009 | Peh et al. |
| 2010/0004506 A1 | 1/2010 | Saadat |
| 2010/0004633 A1 | 1/2010 | Rothe et al. |
| 2010/0004661 A1 | 1/2010 | Verin et al. |
| 2010/0130836 A1 | 5/2010 | Malchano et al. |
| 2011/0021926 A1* | 1/2011 | Spencer ............... A61B 5/6852 600/478 |
| 2011/0060227 A1 | 3/2011 | Saadat |
| 2011/0060298 A1 | 3/2011 | Saadat |
| 2011/0144576 A1 | 6/2011 | Rothe et al. |
| 2011/0196237 A1 | 8/2011 | Pelissier et al. |
| 2012/0016221 A1 | 1/2012 | Saadat et al. |
| 2012/0059366 A1 | 3/2012 | Drews et al. |
| 2012/0095332 A1 | 4/2012 | Nitta et al. |
| 2012/0150046 A1 | 6/2012 | Watson et al. |
| 2013/0172745 A1 | 7/2013 | Choi |
| 2014/0012074 A1 | 1/2014 | Vazales et al. |
| 2015/0094577 A1 | 4/2015 | Saadat et al. |
| 2015/0094582 A1 | 4/2015 | Tanaka et al. |
| 2015/0190036 A1 | 7/2015 | Saadat |
| 2015/0250381 A1 | 9/2015 | Bedard et al. |
| 2015/0366440 A1 | 12/2015 | Rothe et al. |
| 2016/0038005 A1 | 2/2016 | Saadat et al. |
| 2016/0095501 A1 | 4/2016 | Saadat et al. |
| 2016/0227989 A1 | 8/2016 | Saadat et al. |
| 2016/0361040 A1 | 12/2016 | Tanaka et al. |
| 2017/0071460 A1 | 3/2017 | Miller et al. |
| 2018/0000314 A1 | 1/2018 | Saadat et al. |
| 2018/0228350 A1 | 8/2018 | Saadat et al. |
| 2019/0008360 A1 | 1/2019 | Peh et al. |
| 2019/0014975 A1 | 1/2019 | Saadat et al. |
| 2019/0021577 A1 | 1/2019 | Peh et al. |
| 2019/0046013 A1 | 2/2019 | Saadat et al. |
| 2019/0125166 A1 | 5/2019 | Saadat |
| 2019/0307331 A1 | 10/2019 | Saadat et al. |
| 2019/0343373 A1 | 11/2019 | Saadat et al. |
| 2020/0054200 A1 | 2/2020 | Saadat et al. |
| 2020/0069166 A1 | 3/2020 | Miller et al. |
| 2020/0305693 A1 | 10/2020 | Saadat et al. |
| 2021/0007594 A1 | 1/2021 | Miller et al. |
| 2022/0338712 A1 | 10/2022 | Saadat et al. |

FOREIGN PATENT DOCUMENTS

| | | |
|---|---|---|
| EP | 0263661 A2 | 9/1988 |
| EP | 0301288 A1 | 2/1989 |
| EP | 0842673 A1 | 5/1998 |
| JP | S5993413 A | 5/1984 |
| JP | S59181315 A | 10/1984 |
| JP | H01221133 A | 9/1989 |
| JP | H033284265 A | 12/1991 |
| JP | H05103746 A | 4/1993 |
| JP | H06507809 A | 9/1994 |
| JP | H0951897 A | 2/1997 |
| JP | H11299725 A | 11/1999 |
| JP | 2001504363 A | 4/2001 |
| JP | 2001258822 A | 9/2001 |
| WO | WO-9221292 A2 | 12/1992 |
| WO | WO-9407413 A1 | 4/1994 |
| WO | WO-9503843 A1 | 2/1995 |
| WO | WO-9740880 A1 | 11/1997 |
| WO | WO-9818388 A1 | 5/1998 |
| WO | WO-0024310 A1 | 5/2000 |
| WO | WO-0149356 A1 | 7/2001 |
| WO | WO-0172368 A2 | 10/2001 |
| WO | WO-0230310 A1 | 4/2002 |
| WO | WO-03037416 A1 | 5/2003 |
| WO | WO-03039350 A2 | 5/2003 |
| WO | WO-03053491 A2 | 7/2003 |
| WO | WO-03073942 A2 | 9/2003 |
| WO | WO-03101287 A2 | 12/2003 |
| WO | WO-2004043272 A1 | 5/2004 |
| WO | WO-2004080508 A2 | 9/2004 |
| WO | WO-2005070330 A1 | 8/2005 |
| WO | WO-2005077435 A1 | 8/2005 |
| WO | WO-2005081202 A1 | 9/2005 |
| WO | WO-2006017517 A2 | 2/2006 |
| WO | WO-2006024015 A1 | 3/2006 |
| WO | WO-2006083794 A2 | 8/2006 |

(56) References Cited

FOREIGN PATENT DOCUMENTS

| WO | WO-2006091597 A1 | 8/2006 |
|---|---|---|
| WO | WO-2006126979 A2 | 11/2006 |
| WO | WO-2007067323 A2 | 6/2007 |
| WO | WO-2007079268 A2 | 7/2007 |
| WO | WO-2007133845 A2 | 11/2007 |
| WO | WO-2007134258 A2 | 11/2007 |
| WO | WO-2008015625 A2 | 2/2008 |
| WO | WO-2008021994 A2 | 2/2008 |
| WO | WO-2008021997 A2 | 2/2008 |
| WO | WO-2008021998 A2 | 2/2008 |
| WO | WO-2008024261 A2 | 2/2008 |
| WO | WO-2008079828 A2 | 7/2008 |
| WO | WO-2009112262 A2 | 9/2009 |

OTHER PUBLICATIONS

Avitall B., et al., "Right-Sided Driven Atrial Fibrillation in a Sterile Pericarditis Dog Model," Pacing and Clinical Electrophysiology, 1994, vol. 17, pp. 774.
Avitall, "Vagally Mediated Atrial Fibrillation in a Dog Model can be Ablated by Placing Linear Radiofrequency Lesions at the Junction of the Right Atrial Appendage and the Superior Vena Cava," Pacing and Clinical Electrophysiology, 1995, vol. 18, pp. 857.
Avitall, et al, "A Catheter System to Ablate Atrial Fibrillation in a Sterile Pericarditis Dog Model," Pacing and Clinical Electrophysiology, 1994, vol. 17, pp. 774.
Baker B.M., et al., "Nonpharmacologic Approaches to the Treatment of Atrial Fibrillation and Atrial Flutter," Journal of Cardiovascular Electrophysiology, 1995, vol. 6 (10 Pt 2), pp. 972-978.
Bhakta D., et al., "Principles of Electroanatomic Mapping," Indian Pacing and Electrophysiology Journal, 2008, vol. 8 (1), pp. 32-50.
Bidoggia H., et al., "Transseptal Left Heart Catheterization: Usefulness of the Intracavitary Electrocardiogram in the Localization of the Fossa Ovalis," Cathet Cardiovasc Diagn, 1991, vol. 24 (3), pp. 221-225, PMID: 1764747 [online], [Retrieved Feb. 15, 2010], Retrieved from the Internet:< URL: http://www.ncbi.nlm.nih.gov/sites/entrez>.
Bredikis J.J., et al., "Surgery of Tachyarrhythmia: Intracardiac Closed Heart Cryoablation," Pacing and Clinical Electrophysiology, 1990, vol. 13 (Part 2), pp. 1980-1984.
Communication from the Examining Division for Application No. EP08734083.6 dated Nov. 12, 2010, 3 pages.
Communication from the Examining Division for Application No. EP06734083.6 dated Oct. 23, 2009, 1 pages.
Comunication from the Examining Division for Application No. EP08746822.9 dated Jul. 13, 2010, 1 page.
Co-pending U.S. Appl. No. 61/286,283, filed Dec. 14, 2009.
Co-pending U.S. Appl. No. 61/297,462, filed Jan. 22, 2010.
Cox J.L., "Cardiac Surgery for Arrhythmias," Journal of Cardiovascular Electrophysiology, 2004, vol. 15, pp. 250-262.
Cox J.L., "The Status of Surgery for Cardiac Arrhythmias," Circulation, 1985, vol. 71, pp. 413-417.
Cox J.L., "The Surgical Treatment of Atrial Fibrillation," The Journal of Thoracic and Cardiovascular Surgery, 1991, vol. 101, pp. 584-592.
Cox J.L., et al., "Five-Year Experience With the Maze Procedure for Atrial Fibrillation," The Annals of Thoracic Surgery, 1993, vol. 56, pp. 814-824.
Cox J.L., et al., "Modification of the Maze Procedure for Atrial Flutter and Atrial Fibrillation," The Journal of Thoracic and Cardiovascular Surgery, 1995, vol. 110, pp. 473-484.
Elvan A., et al., "Radiofrequency Catheter Ablation (RFCA) of the Atria Effectively Abolishes Pacing Induced Chronic Atrial Fibrillation," Pacing and Clinical Electrophysiology, 1995, vol. 18, pp. 856.
Elvan A., et al., "Radiofrequency Catheter Ablation of the Atria Reduces Inducibility and Duration of Atrial Fibrillation in Dogs,"
Circulation, vol. 91, 1995, pp. 2235-2244 [online], [retrieved Feb. 4, 2013]. Retrieved from the Internet:< URL: http://circ.ahajournals.org/cgi/content/full/91/8/2235>.
Elvan, et al., "Replication of the 'Maze' Procedure by Radiofrequency Catheter Ablation Reduces the Ability to Induce Atrial Fibrillation," Pacing and Clinical Electrophysiology, 1994, vol. 17, pp. 774.
European Search Report for Application No. EP07799466.3 dated Nov. 18, 2010, 9 pages.
European Search Report for Application No. EP08746822.9 dated Mar. 29, 2010, 7 Pages.
Examination Communication for Application No. EP06734083.6 dated May 18, 2010, 3 Pages.
Extended European Search Report for Application No. EP06734083.6 dated Jul. 1, 2009.
Extended European search report for Application No. EP20070758716 dated Feb. 28, 2011, 8 Pages.
Extended European search report for Application No. EP20070799466 dated Nov. 18, 2010, 9 Pages.
Fieguth H.G., et al., "Inhibition of Atrial Fibrillation by Pulmonary Vein Isolation and Auricular Resection—Experimental Study in a Sheep Model," The European Journal of Cardio-Thoracic Surgery, 1997, vol. 11, pp. 714-721.
Final Office Action dated Mar. 1, 2010 for U.S. Appl. No. 12/117,655, filed May 8, 2008.
Final Office Action dated Jun. 2, 2011 for U.S. Appl. No. 12/117,655, filed May 8, 2008.
Final Office Action dated Oct. 5, 2010 for U.S. Appl. No. 11/810,850, filed Jun. 7, 2007.
Final Office Action dated May 12, 2011 for U.S. Appl. No. 11/775,771, filed Jul. 10, 2007.
Final Office Action dated Sep. 16, 2010 for U.S. Appl. No. 11/828,267, filed Jul. 25, 2007.
Hoey M.F., et al., "Intramural Ablation Using Radiofrequency Energy Via Screw-Tip Catheter and Saline Electrode," Pacing and Clinical Electrophysiology, 1995, vol. 18, Part II, 487.
Huang, "Increase in the Lesion Size and Decrease in the Impedance Rise with a Saline Infusion Electrode Catheter for Radiofrequency," Circulation, 1989, vol. 80 (4), II-324.
International Search Report and Written Opinion for Application No. PCT/US2007/073184, dated Aug. 12, 2012, 7 pages.
International Search Report for Application No. PCT/US2006/003288, dated Aug. 9, 2007, 1 page.
International Search Report for Application No. PCT/US2007/064195, dated Dec. 7, 2007, 1 page.
International Search Report for Application No. PCT/US2007/071226, dated Sep. 4, 2006, 1 page.
International Search Report for Application No. PCT/US2007/077429, dated Apr. 7, 2008, 1 page.
Moser K.M., et al., "Angioscopic Visualization of Pulmonary Emboli," Chest, 1980, vol. 77 (2), pp. 198-201.
Nakamura F., et al., "Percutaneous Intracardiac Surgery With Cardioscopic Guidance," SPIE, 1992, vol. 1642, pp. 214-216.
Non-Final Office Action dated Jun. 7, 2011 for U.S. Appl. No. 12/323,281, filed Nov. 25, 2008.
Non-Final Office Action dated Aug. 8, 2011 for U.S. Appl. No. 12/464,800, filed May 12, 2009.
Non-Final Office Action dated Jun. 8, 2011 for U.S. Appl. No. 12/117,655, filed May 85, 2008.
Non-Final Office Action dated May 9, 2011 for U.S. Appl. No. 11/961,950, filed Dec. 20, 2007.
Non-Final Office Action dated May 9, 2011 for U.S. Appl. No. 11/961,995, filed Dec. 20, 2007.
Non-Final Office Action dated May 9, 2011 for U.S. Appl. No. 11/962,029, filed Dec. 20, 2007.
Non-Final Office Action dated Jun. 10, 2010 for U.S. Appl. No. 11/560,742, filed Nov. 16, 2006.
Non-Final Office Action dated Apr. 11, 2011 for U.S. Appl. No. 11/763,399, filed Jun. 14, 2007.
Non-Final Office Action dated Mar. 11, 2011 for U.S. Appl. No. 11/848,202, filed Aug. 30, 2007.
Non-Final Office Action dated May 11, 2011 for U.S. Appl. No. 11/828,267, filed Jul. 25, 2007.

(56) References Cited

OTHER PUBLICATIONS

Non-Final Office Action dated Apr. 12, 2011 for U.S. Appl. No. 12/499,011, filed Jul. 7, 2009.
Non-Final Office Action dated Jan. 14, 2010 for U.S. Appl. No. 11/828,267, filed Jul. 25, 2007.
Non-Final Office Action dated Dec. 16, 2010 for U.S. Appl. No. 12/117,655, filed May 8, 2008.
Non-Final Office Action dated Mar. 16, 2010 for U.S. Appl. No. 11/810,850, filed Jun. 7, 2007.
Non-Final Office Action dated Feb. 18, 2011 for U.S. Appl. No. 12/947,198, filed Nov. 16, 2010.
Non-Final Office Action dated Feb. 18, 2011 for U.S. Appl. No. 12/947,246, filed Nov. 16, 2006.
Non-Final Office Action dated May 20, 2011 for U.S. Appl. No. 11/775,819, filed Jul. 10, 2007.
Non-Final Office Action dated May 20, 2011 for U.S. Appl. No. 11/877,386, filed Oct. 23, 2007.
Non-Final Office Action dated Jul. 21, 2010 for U.S. Appl. No. 11/687,597, filed Mar. 16, 2007.
Non-Final Office Action dated Apr. 22, 2011 for U.S. Appl. No. 12/367,019, filed Feb. 6, 2009.
Non-Final Office Action dated May 23, 2011 for U.S. Appl. No. 11/775,837, filed Jul. 10, 2007.
Non-Final Office Action dated Nov. 24, 2010 for U.S. Appl. No. 11/848,429, filed Aug. 31, 2007.
Non-Final Office Action dated Nov. 24, 2010 for U.S. Appl. No. 12/464,800, filed May 12, 2009.
Non-Final Office Action dated Apr. 25, 2011 for U.S. Appl. No. 11/959,156, filed Dec. 18, 2007.
Non-Final Office Action dated Feb. 25, 2010 for U.S. Appl. No. 11/259,498, filed Oct. 25, 2005.
Non-Final Office Action dated Feb. 25, 2011 for U.S. Appl. No. 11/848,207, filed Aug. 30, 2007.
Non-Final Office Action dated Apr. 26, 2011 for U.S. Appl. No. 11/848,532, filed Aug. 31, 2007.
Non-Final Office Action dated Apr. 27, 2011 for U.S. Appl. No. 11/828,281, filed Jul. 25, 2007.
Non-Final Office Action dated Aug. 27, 2010 for U.S. Appl. No. 11/775,771, filed Jul. 10, 2007.
Non-Final Office Action dated Dec. 27, 2010 for U.S. Appl. No. 12/026,455, filed Feb. 5, 2008.
Notice of Allowance dated Feb. 3, 2011 for U.S. Appl. No. 11/560,732, filed Nov. 16, 2006.
Notice of Allowance dated Jun. 13, 2011 for Japanese Application No. 2007-554156 filed Jan. 30, 2006.
Notice of Allowance dated Nov. 15, 2010 for U.S. Appl. No. 11/259,498, filed Oct. 25, 2005.
Notice of Allowance dated Nov. 15, 2010 for U.S. Appl. No. 11/560,742, filed Nov. 16, 2006.
Notice of Allowance dated Feb. 24, 2011 for U.S. Appl. No. 11/560,732, filed Mar. 16, 2007.
Notice of Allowance dated Feb. 24, 2011 for U.S. Appl. No. 11/587,597, filed Mar. 16, 2007.
Office Action dated Feb. 15, 2011 for Japanese Application No. 2007-554156 filed Jan. 30, 2006.
Office Action dated Apr. 27, 2011 for Japanese Application No. 2009-500630 filed Mar. 16, 2007.
Pappone C., et al., "Circumferential Radiofrequency Ablation of Pulmonary Vein Ostia," Circulation, 2000, vol. 102, pp. 2619-2626.
Sethi K.K., et al., "Transseptal catherization for the electrophysiologist: modification with a 'view'," Journal of Interventional Cardiac Electrophysiology, 2001, vol. 5 (1), pp. 97-99.
Supplemental European Search Report for Application No. EP07758716 dated Feb. 28, 2011, 8 Pages.
Supplemental European search report for Application No. EP07812146.4 dated Nov. 18, 2010, 8 Pages.
Supplemental European Search Report for Application No. EP07841754 dated Jun. 30, 2010, 6 pages.
Thiagalingam A., et al., "Cooled Needle Catheter Ablation Creates Deeper and Wider Lesions than Irrigated Tip Catheter Ablation," Journal of Cardiovascular Electrophysiology, 2005, vol. 16 (5), pp. 1-8.
Uchida Y., "Developmental History of Cardioscopes", in: Coronary Angioscopy, Chapter 19, Futura Publishing Company, Inc., 2001, pp. 187-197.
Willkampf F.H., et al., "Radiofrequency Ablation with a Cooled Porous Electrode Catheter," JACC, Abstract, 1988, vol. 11 (2), pp. 17A.
Written Opinion for Application No. PCT/US2006/003288, dated Aug. 9, 2007, 6 pages.
Written Opinion for Application No. PCT/US2007/064195, dated Dec. 7, 2007, 5 pages.
Written Opinion for Application No. PCT/US2007/071226, dated Sep. 4, 2008, 4 pages.
Written Opinion for Application No. PCT/US2007/077429, dated Apr. 7, 2008, 5 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

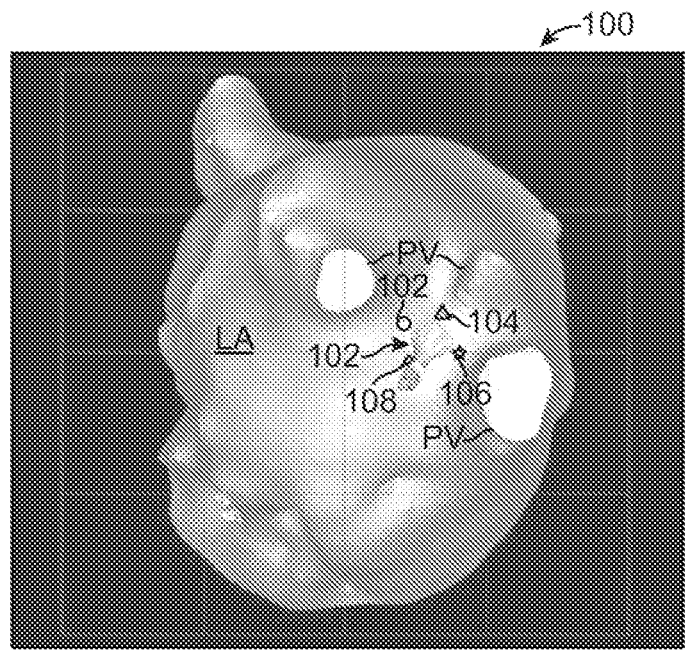
FIG. 7A
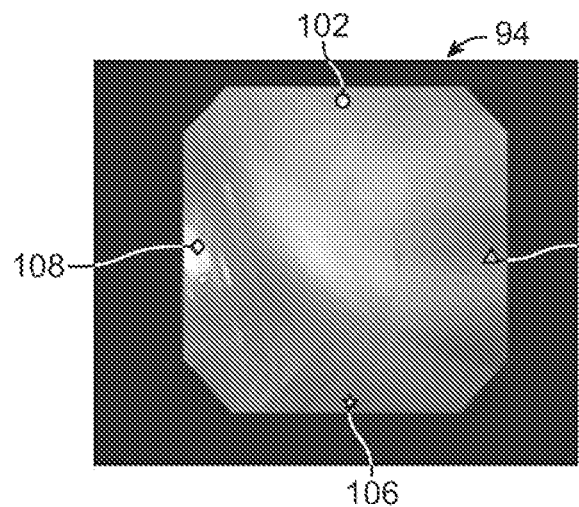 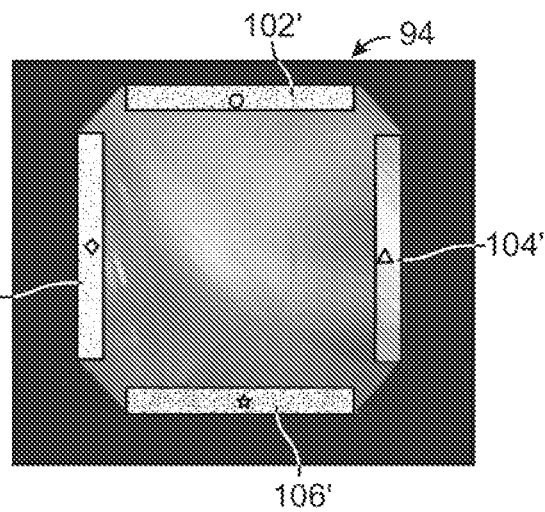
FIG. 7B　　　FIG. 7C

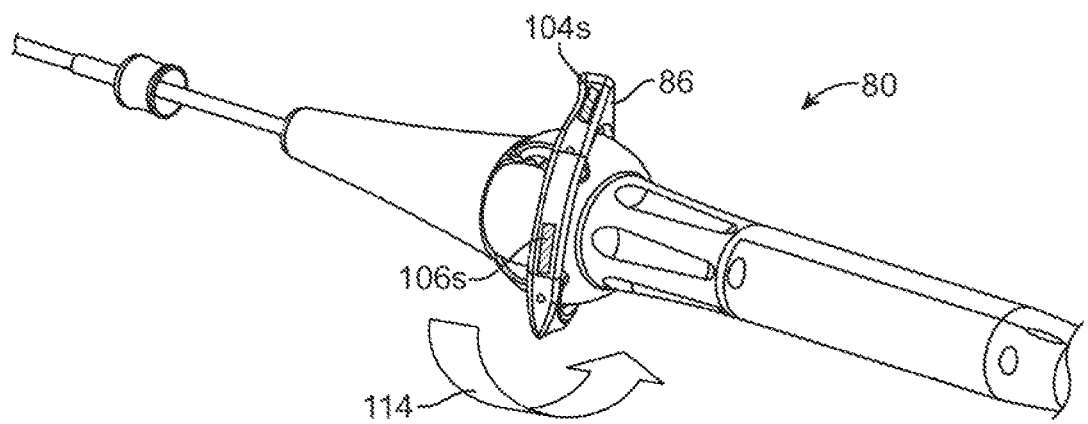
FIG. 10A
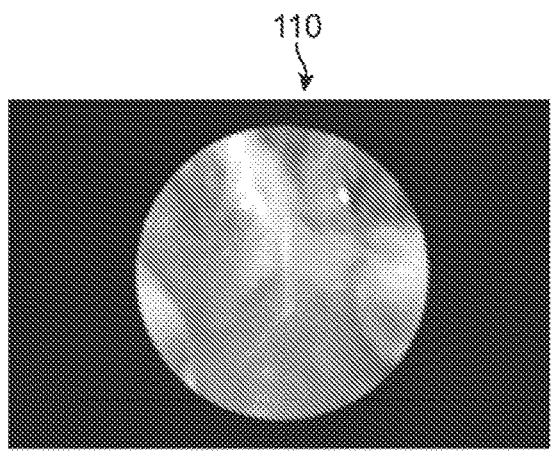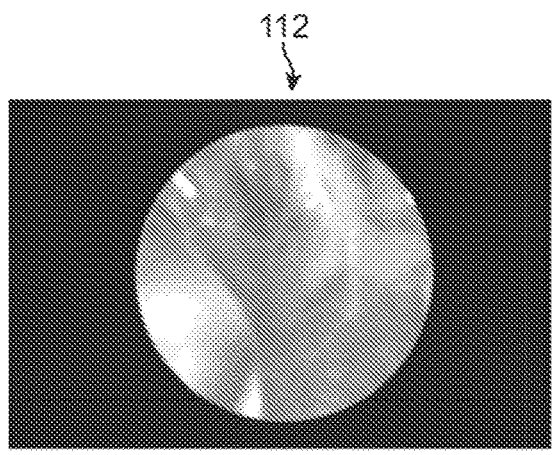
FIG. 10B  FIG. 10C

IN-VIVO VISUALIZATION SYSTEMS

CROSS-REFERENCE TO RELATED APPLICATIONS

This application is a division of U.S. patent application Ser. No. 14/714,992, filed May 18, 2015, which is a continuation of U.S. patent application Ser. No. 12/778,878, filed May 12, 2010 which claims the benefit of priority to U.S. Provisional Patent Application No. 61/177,618 filed May 12, 2009, which is also a continuation-in-part of U.S. patent application Ser. No. 11/763,399 filed Jun. 14, 2007, which claims the benefit of priority to U.S. Provisional Application 60/804,801 filed Jun. 14, 2006; 60/806,924 filed Jul. 10, 2006, 60/806,926 filed Jul. 10, 2006; 60/871,415 filed Dec. 21, 2006; 60/871,424 filed Dec. 21, 2006; and 60/888,242 filed Feb. 5, 2007, which are is incorporated herein by reference in their entireties.

FIELD OF THE INVENTION

The present invention relates generally to medical devices used for visualizing and/or assessing regions of tissue within a body. More particularly, the present invention relates to methods and apparatus for visualizing and/or assessing regions of tissue within a body, such as the chambers of a heart, to facilitate diagnoses and/or treatments for the tissue.

BACKGROUND OF THE INVENTION

Conventional devices for visualizing interior regions of a body lumen are known. For example, ultrasound devices have been used to produce images from within a body in vivo. Ultrasound has been used both with and without contrast agents, which typically enhance ultrasound-derived images.

Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, such imaging balloons have many inherent disadvantages. For instance, such balloons generally require that the balloon be inflated to a relatively large size which may undesirably displace surrounding tissue and interfere with fine positioning of the imaging system against the tissue. Moreover, the working area created by such inflatable balloons are generally cramped and limited in size. Furthermore, inflated balloons may be susceptible to pressure changes in the surrounding fluid. For example, if the environment surrounding the inflated balloon undergoes pressure changes, e.g., during systolic and diastolic pressure cycles in a beating heart, the constant pressure change may affect the inflated balloon volume and its positioning to produce unsteady or undesirable conditions for optimal tissue imaging. Additionally, imaging balloons are subject to producing poor or blurred tissue images if the balloon is not firmly pressed against the tissue surface because of intervening blood between the balloon and tissue.

Accordingly, these types of imaging modalities are generally unable to provide desirable images useful for sufficient diagnosis and therapy of the endoluminal structure, due in part to factors such as dynamic forces generated by the natural movement of the heart. Moreover, anatomic structures within the body can occlude or obstruct the image acquisition process. Also, the presence and movement of opaque bodily fluids such as blood generally make in vivo imaging of tissue regions within the heart difficult. Moreover, once a visual image of a tissue region is acquired in vivo, there may be additional difficulties in assessing the condition of the underlying tissue for appropriate treatments or treatment parameters.

Thus, a tissue imaging system which is able to provide real-time in vivo images and assessments of tissue regions within body lumens such as the heart through opaque media such as blood and which also provide instruments for therapeutic procedures upon the visualized tissue are desirable.

SUMMARY OF THE INVENTION

In describing the tissue imaging and manipulation apparatus that may be utilized for procedures within a body lumen, such as the heart, in which visualization of the surrounding tissue is made difficult, if not impossible, by medium contained within the lumen such as blood, is described below. Generally, such a tissue imaging and manipulation apparatus comprises an optional delivery catheter or sheath through which a deployment catheter and imaging hood may be advanced for placement against or adjacent to the tissue to be imaged.

The deployment catheter may define a fluid delivery lumen therethrough as well as an imaging lumen within which an optical imaging fiber or assembly may be disposed for imaging tissue. When deployed, the imaging hood may be expanded into any number of shapes, e.g., cylindrical, conical as shown, semi-spherical, etc., provided that an open area or field is defined by the imaging hood. The open area is the area through which the tissue region of interest may be imaged. Additionally, the tissue may be viewed not only through the aperture but also through the distal membrane. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control The deployment catheter may also be stabilized relative to the tissue surface through various methods. For instance, inflatable stabilizing balloons positioned along a length of the catheter may be utilized, or tissue engagement anchors may be passed through or along the deployment catheter for temporary engagement of the underlying tissue.

In operation, after the imaging hood has been deployed, fluid may be pumped at a positive pressure through the fluid delivery lumen until the fluid fills the open area completely and displaces any blood from within the open area. The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

In an exemplary variation for imaging tissue surfaces within a heart chamber containing blood, the tissue imaging and treatment system may generally comprise a catheter body having a lumen defined therethrough, a visualization element disposed adjacent the catheter body, the visualization element having a field of view, a transparent or translucent fluid source in fluid communication with the lumen, and a barrier or membrane extendable from the catheter body to localize, between the visualization element and the field of view, displacement of blood by transparent fluid that flows from the lumen, and an instrument translatable through the displaced blood for performing any number of treatments upon the tissue surface within the field of view. The imaging hood may be formed into any number of configurations and the imaging assembly may also be utilized with any number of therapeutic tools which may be deployed through the deployment catheter.

More particularly in certain variations, the tissue visualization system may comprise components including the imaging hood, where the hood may further include a membrane having a main aperture and additional optional openings disposed over the distal end of the hood. An introducer sheath or the deployment catheter upon which the imaging hood is disposed may further comprise a steerable segment made of multiple adjacent links which are pivotably connected to one another and which may be articulated within a single plane or multiple planes. The deployment catheter itself may be comprised of a multiple lumen extrusion, such as a four-lumen catheter extrusion, which is reinforced with braided stainless steel fibers to provide structural support. The proximal end of the catheter may be coupled to a handle for manipulation and articulation of the system.

To provide visualization, an imaging element such as a fiberscope or electronic imager such as a solid state camera, e.g., CCD or CMOS, may be mounted, e.g., on a shape memory wire, and positioned within or along the hood interior. A fluid reservoir and/or pump (e.g., syringe, pressurized intravenous bag, etc.) may be fluidly coupled to the proximal end of the catheter to hold the translucent fluid such as saline or contrast medium as well as for providing the pressure to inject the fluid into the imaging hood.

In clearing the hood of blood and/or other bodily fluids, it is generally desirable to purge the hood in an efficient manner by minimizing the amount of clearing fluid, such as saline, introduced into the hood and thus into the body. As excessive saline delivered into the blood stream of patients with poor ventricular function may increase the risk of heart failure and pulmonary edema, minimizing or controlling the amount of saline discharged during various therapies, such as atrial fibrillation ablation, atrial flutter ablation, transseptal puncture, etc. may be generally desirable.

Steering of the hood assembly via controls on the handle may present some difficulties particularly when the catheter assembly has been contorted into various configurations by patient anatomies. This contortion may result in a mismatch between the steering controls and the corresponding movement on the screen of the in-vivo visualization system potentially leading to the user having to make constant micro movements on the steering controls to mentally re-map the direction of movement on the screen to the steering controls. This constant readjustment increases procedure times and may put undue stress and frustration on the user performing the treatment. This may continue to exist even with the addition of three-dimensional visualization systems as the movement of the catheter hood may not correspond to the real-time images viewed on the screen projecting the tissue images. Directional indicators on the visualization screen, in-vivo visualization screen, as well as on the steering controls may help to give the user a sense of orientation of the catheter device with respect to the in-vivo image being viewed. With this sense of orientation, users of the catheter device may be intuitively aware of the direction in which they should manipulate the tip of the device in order to access a specific region of anatomy.

In order to help physicians gain a better sense of the catheter hood orientation, color coded directional indicators, e.g., illustrated as dots or other symbols, may used to represent a specific section of the catheter hood. At least one of these color coded dots or symbols may be placed on a representation of the catheter assembly on the monitor, on the in vivo visualization monitor, and on the steering controls of the catheter handle. For illustrative purposes, the dots or symbols (which may also be optionally color-coded) may represent one of four directional indicators which may be represented on the monitors.

In yet another variation, one or more of the directional indicators located on the handle assembly may be configured as tactile sensors. When a user places their hand or finger upon one of the tactile sensors, the corresponding directional indicator displayed on the positional image may begin to blink, flash, or otherwise provide some indication that the corresponding direction on the control handle has been activated thus giving the user an immediate indication as to which portion of the handle control to manipulate without having to move their eyes from the monitors. The touch-sensitive sensors located on the handle assembly may be configured as touch-sensitive sensors utilizing any number of known mechanisms, such as capacitive sensors or pressure-sensitive sensors, etc.

Aside from the use of directional indicators and generated positional information, other mechanisms may be utilized for making the manipulation and steering of the hood relative to the body more intuitive. One example may utilize rotation of the image on the monitor showing the visualized tissue to affix a direction on the monitor to a direction of mechanical actuation on the control handle depending upon how the handle is re-orientated. In another variation, rather than rotating the images of the tissue based on the movement and rotation of the catheter handle, the images of the tissue may be fixed and the steering controls instead may be remapped.

In yet another variation for facilitating tissue treatment, the captured visual image of the tissue as imaged through the hood may be projected and mapped to the representative map of the tissue anatomy. Being able to visualize the "active spot" that is being visualized through the hood by mapping it onto the surface of the representative three-dimensional model may allow the physician to more accurately navigate the anatomy. When visualizing and treating tissue using the visualization system, the catheter hood may not necessarily be visualizing the tissue that is seen on the in vivo visualization system. This may occur due to a variety of reasons such as non-perpendicularity of the hood to the tissue surface or contortion of the hood. Because the active spot moves as the catheter hood is being moved, this may give the physician a greater awareness and confidence on both the visualization systems.

In yet another example, way-pointing methods may also be utilized to facilitate tissue treatment by the physician. Way-pointing is a pre-operative method that allows the physician to map out the ablation procedure by selecting lesion sites on the three-dimensional model of the anatomy. This data may be then transmitted to the catheter system which may generate and project approximated lesion boundaries to be formed as well as the navigational information to guide the hood from one lesion to another as the procedure progresses. Such a way-pointing system may prevent the user from becoming disoriented in the anatomy of the heart and may effectively speed procedure times while ensuring that lesions are contiguously formed, if necessary or desired, by showing lesion boundaries.

Additionally and/or alternatively, other methods for helping the user to maintain spatial awareness of the surrounding tissue and anatomical features may also be utilized for facilitating navigation, safety, procedure efficacy, etc. The features to be displayed may be pre-selected on the three-dimensional visualization model prior to treatment. These points of interest may allow the user to establish a base of reference when they are viewing the images of tissue on the monitor. Additionally, the indication of surrounding tissue regions may help to ensure the avoidance of inadvertently treating tissue surrounding the tissue region of interest.

Yet another example for facilitating tissue treatment procedures may utilize the augmentation of images utilizing previously captured images. For instance, captured images previously visualized through the hood and recorded may be compiled and stitched relative to one another to provide a seamless interior map of the anatomy. This image stitching may present an actual map of the interior of the heart instead of an approximate three-dimensional model. Moreover, the images can also be mapped such that they take on the contours of the model. Being able to see the actual visual inside the heart may increase physician confidence and also the speed of the procedure.

Procedure guidance systems are particularly useful when the user may be unfamiliar with the device and its capabilities or wish to facilitate the procedure by minimizing steering decisions from one ablation point to another. Such a system may function by first allowing the user to select potential ablation sites, e.g., in proximity to a pulmonary vein ostium, on either a pre-operative three-dimensional model or on a uniquely generated three-dimensional model. Physicians can then navigate the catheter hood into the particular orientation before performing ablation. Additionally, for steerable sections with a plurality of sensors, the steerable section can be graphically represented as well.

BRIEF DESCRIPTION OF THE DRAWINGS

FIG. 7A shows a representative image of a hood assembly positioned within a generated three-dimensional model of the left atrial chamber of a heart in proximity to the pulmonary veins.

FIGS. 7B and 7C show captured tissue images visualized through the hood with directional indicators superimposed upon the images.

FIGS. 10A to 10C show an example of a perspective view of a handle assembly manipulated in a first direction to move an imaged region, respectively.

DETAILED DESCRIPTION OF THE INVENTION

Reconfiguring a tissue visualization and treatment device from a low profile delivery configuration for intravascular delivery through the vessels of a patient to a deployed and expanded configuration may subject the distal end effector used for visualization and/or treatment, such as energy delivery, to potentially severe mechanical stresses (e.g., torsion, compression, tension, shearing, etc.). For example, a reconfigurable hood which undergoes a shape change from its collapsed configuration to an expanded conical shape may utilize a distensible, collapsible, and/or reconfigurable substrate which may utilize electrode placement and electrical connection assemblies which are robust and able to withstand such stresses. Such electrical connection assemblies may be shielded or insulated from contacting other structures so as to present a smooth or unobstructive profile for reconfiguring with the hood.

Turning now to the tissue-imaging and manipulation apparatus, such an apparatus may have one or more electrodes positioned thereon and also provide real-time images in vivo of tissue regions within a body lumen such as a heart, which is filled with blood flowing dynamically therethrough. The apparatus is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures.

Figure 1A:
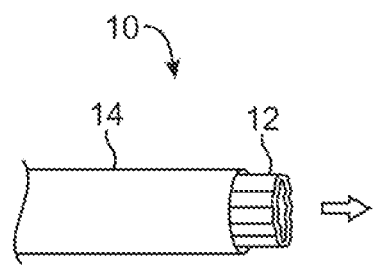
FIG. 1A shows a side view of one variation of a tissue imaging apparatus during deployment from a sheath or delivery catheter.
Figure 1B:
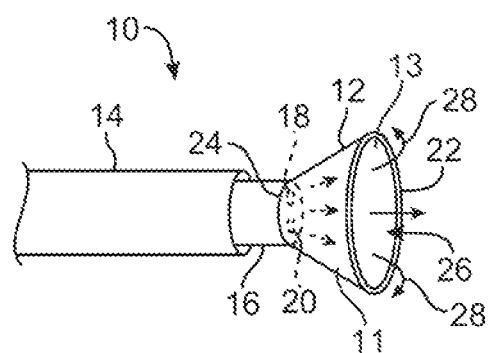
FIG. 1B shows the deployed tissue imaging apparatus of FIG. 1A having an optionally expandable hood or sheath attached to an imaging and/or diagnostic catheter.
Figure 1C:
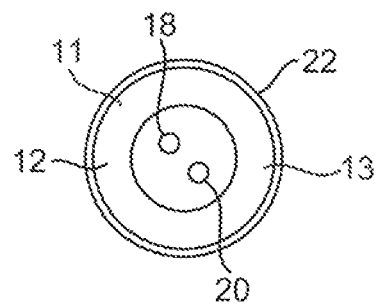
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, DE), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 2A:
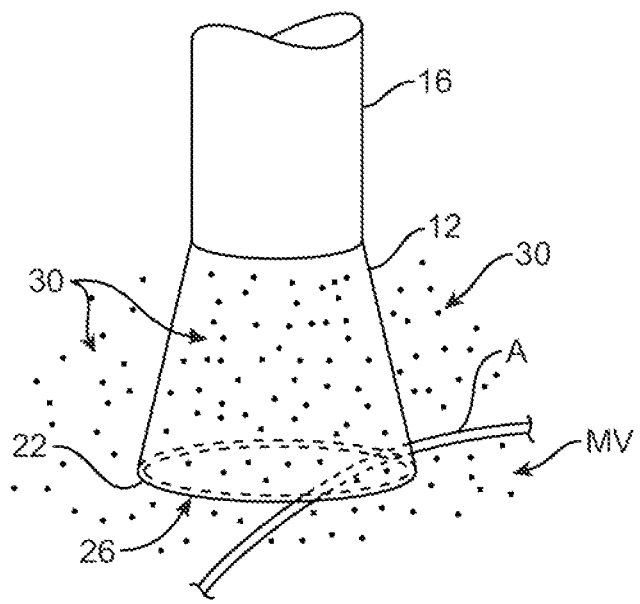
FIGS. 2A and 2B show one example of a deployed tissue imager positioned against or adjacent to the tissue to be imaged and a flow of fluid, such as saline, displacing blood from within the expandable hood.
Figure 2B:
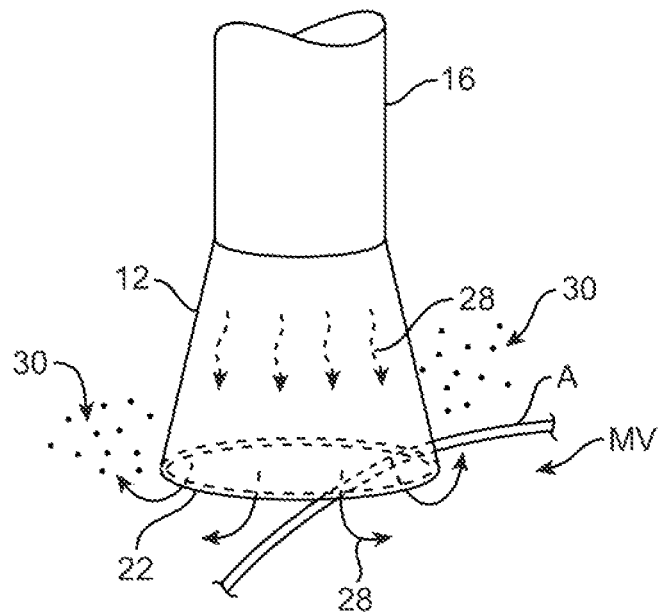

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
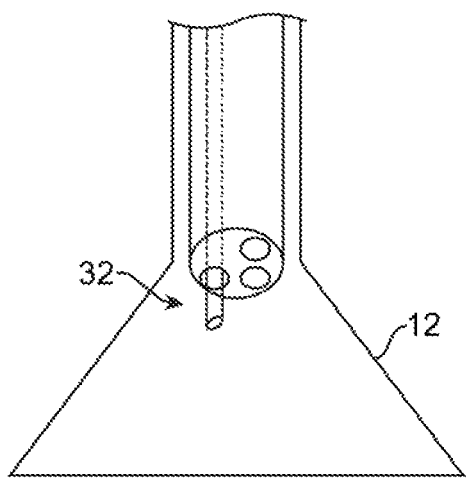
FIGS. 3A and 3B show examples of various visualization imagers which may be utilized within or along the imaging hood.
Figure 3B:
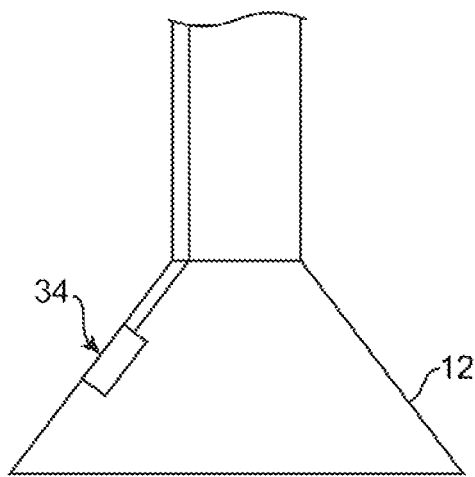

FIG. 3A shows a partial cross-sectional view of an example where one or more optical fiber bundles 32 may be positioned within the catheter and within imaging hood 12 to provide direct in-line imaging of the open area within hood 12. FIG. 3B shows another example where an imaging element 34 (e.g., CCD or CMOS electronic imager) may be placed along an interior surface of imaging hood 12 to provide imaging of the open area such that the imaging element 34 is off-axis relative to a longitudinal axis of the hood 12, as described in further detail below. The off-axis position of element 34 may provide for direct visualization and uninhibited access by instruments from the catheter to the underlying tissue during treatment. Additionally and/or alternatively, the electronic imaging element 34 (e.g., CCD or CMOS) may also be positioned along or in proximity to the longitudinal axis of the catheter to provide in-line imaging of the open area.

Figure 4A:
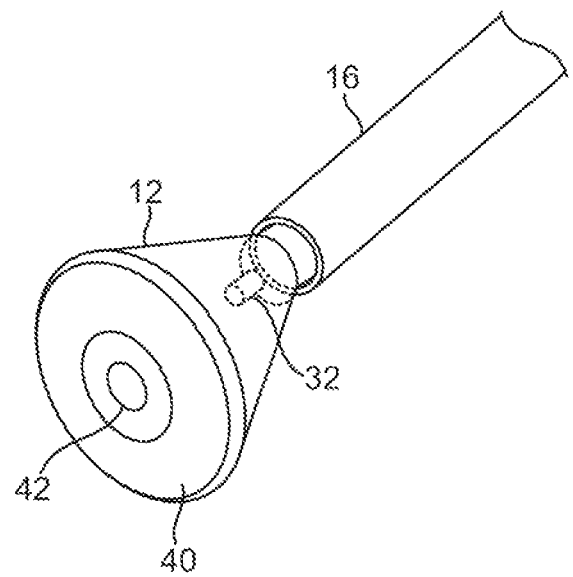
FIGS. 4A and 4B show perspective and end views, respectively, of an imaging hood having at least one layer of a transparent elastomeric membrane over the distal opening of the hood.
Figure 4B:
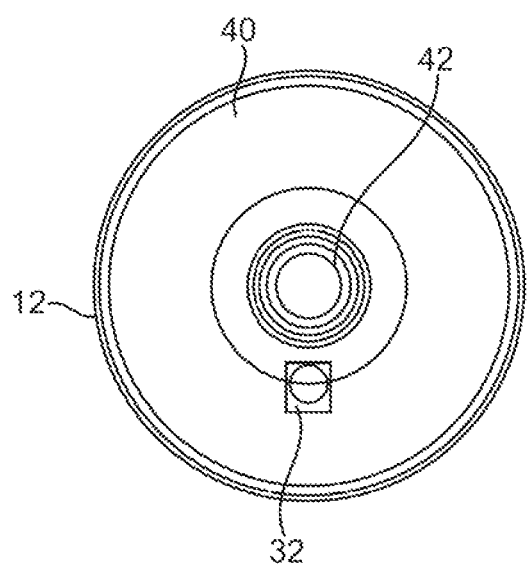

In utilizing the imaging hood 12 in any one of the procedures described herein, the hood 12 may have an open field which is uncovered and clear to provide direct tissue contact between the hood interior and the underlying tissue to effect any number of treatments upon the tissue, as described above. Yet in additional variations, imaging hood 12 may utilize other configurations. An additional variation of the imaging hood 12 is shown in the perspective and end views, respectively, of FIGS. 4A and 4B, where imaging hood 12 includes at least one layer of a transparent elastomeric membrane 40 over the distal opening of hood 12. An aperture 42 having a diameter which is less than a diameter of the outer lip of imaging hood 12 may be defined over the center of membrane 40 where a longitudinal axis of the hood 12 intersects the membrane such that the interior of hood 12 remains open and in fluid communication with the environment external to hood 12. Furthermore, aperture 42 may be sized, e.g., between 1 to 2 mm or more in diameter and membrane 40 can be made from any number of transparent elastomers such as silicone, polyurethane, latex, etc. such that contacted tissue may also be visualized through membrane 40 as well as through aperture 42.

Aperture 42 may function generally as a restricting passageway to reduce the rate of fluid out-flow from the hood 12 when the interior of the hood 12 is infused with the clear fluid through which underlying tissue regions may be visualized. Aside from restricting out-flow of clear fluid from within hood 12, aperture 42 may also restrict external surrounding fluids from entering hood 12 too rapidly. The reduction in the rate of fluid out-flow from the hood and blood in-flow into the hood may improve visualization conditions as hood 12 may be more readily filled with transparent fluid rather than being filled by opaque blood which may obstruct direct visualization by the visualization instruments.

Moreover, aperture 42 may be aligned with catheter 16 such that any instruments (e.g., piercing instruments, guidewires, tissue engagers, etc.) that are advanced into the hood interior may directly access the underlying tissue uninhibited or unrestricted for treatment through aperture 42. In other variations wherein aperture 42 may not be aligned with catheter 16, instruments passed through catheter 16 may still access the underlying tissue by simply piercing through membrane 40.

Figure 5A:
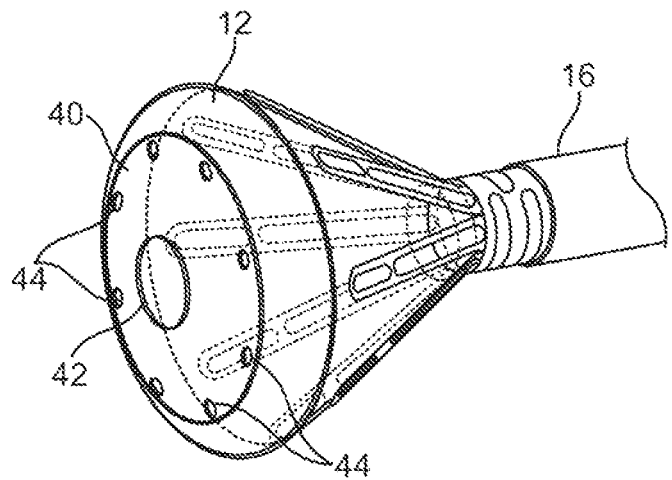
FIGS. 5A and 5B show perspective and end views, respectively, of an imaging hood which includes a membrane with an aperture defined therethrough and a plurality of additional openings defined over the membrane surrounding the aperture.
Figure 5B:
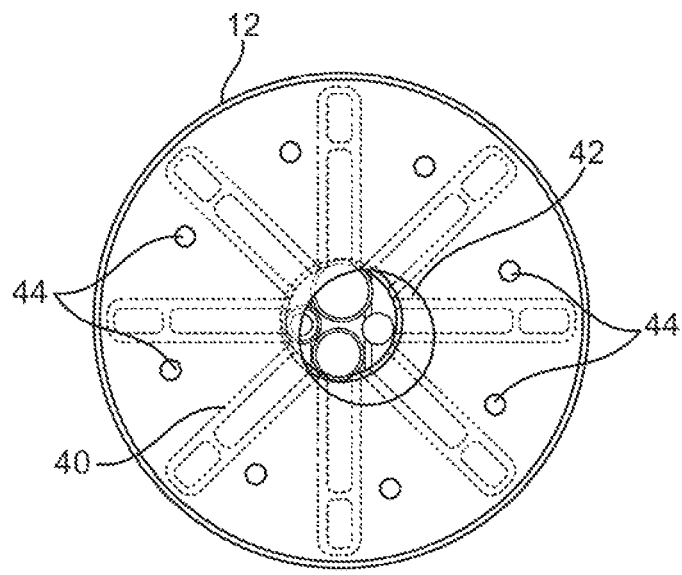

In an additional variation, FIGS. 5A and 5B show perspective and end views, respectively, of imaging hood 12 which includes membrane 40 with aperture 42 defined therethrough, as described above. This variation includes a plurality of additional openings 44 defined over membrane 40 surrounding aperture 42. Additional openings 44 may be uniformly sized, e.g., each less than 1 mm in diameter, to allow for the out-flow of the translucent fluid therethrough when in contact against the tissue surface. Moreover, although openings 44 are illustrated as uniform in size, the openings may be varied in size and their placement may also be non-uniform or random over membrane 40 rather than uniformly positioned about aperture 42 in FIG. 5B. Furthermore, there are eight openings 44 shown in the figures although fewer than eight or more than eight openings 44 may also be utilized over membrane 40.

Additional details of tissue imaging and manipulation systems and methods which may be utilized with apparatus and methods described herein are further described, for example, in U.S. patent application Ser. No. 11/259,498 filed Oct. 25, 2005 (U.S. Pat. Pub. 2006/0184048 A1), which is incorporated herein by reference in its entirety.

In utilizing the devices and methods above, various procedures may be accomplished. One example of such a procedure is crossing a tissue region such as in a transseptal procedure where a septal wall is pierced and traversed, e.g., crossing from a right atrial chamber to a left atrial chamber in a heart of a subject. Generally, in piercing and traversing a septal wall, the visualization and treatment devices described herein may be utilized for visualizing the tissue region to be pierced as well as monitoring the piercing and access through the tissue. Details of transseptal visualization catheters and methods for transseptal access which may be utilized with the apparatus and methods described herein are described in U.S. patent application Ser. No. 11/763,399 filed Jun. 14, 2007 (U.S. Pat. Pub. 2007/0293724 A1), which is incorporated herein by reference in its entirety. Additionally, details of tissue visualization and manipulation catheter which may be utilized with apparatus and methods described herein are described in U.S. patent application Ser. No. 11/259,498 filed Oct. 25, 2005 (U.S. Pat. Pub. 2006/0184048 A1), which is incorporated herein by reference in its entirety.

In clearing the hood of blood and/or other bodily fluids, it is generally desirable to purge the hood in an efficient manner by minimizing the amount of clearing fluid, such as saline, introduced into the hood and thus into the body. As excessive saline delivered into the blood stream of patients with poor ventricular function may increase the risk of heart failure and pulmonary edema, minimizing or controlling the amount of saline discharged during various therapies, such as atrial fibrillation ablation, atrial flutter ablation, transseptal puncture, etc. may be generally desirable.

Turning now to the electrode assemblies and connection systems utilized with the collapsible hood, various examples are described herein which illustrate variations for electrode positioning along the hood which may minimize or reduce the degree of stress imparted to the electrode assemblies. These electrodes (e.g., electrode pairs) may be used to deliver electrical energy such as radio-frequency energy to tissue in direct contact with or in proximity to the electrodes to form lesions upon the tissue surface as well as underlying tissue regions. Additionally, the electrodes or electrode pairs may be positioned about the hood in a uniform or non-uniform manner depending upon the desired configuration. Moreover, these electrodes may also be used to deliver energy into and/or through the purging fluid which may contact the electrodes for conducting the energy through the fluid and into the underlying tissue region being treated. Alternatively, one or more of these electrodes may also be used to detect and/or measure any electrophysiological activity of the contacted tissue prior to, during, or after tissue treatment.

While specific examples of the visualization and treatment hood are shown herein, other variations and examples of hoods and tissue treatment systems may be utilized with the devices and methods described herein. For example, the hoods, systems, and other features as described in Ser. No. 11/259,498 filed Oct. 25, 2005 (U.S. Pat. Pub. 2006/0184048 A1); Ser. No. 11/775,837 filed Jul. 10, 2007 (U.S. Pat. Pub. 2008/0009747 A1); Ser. No. 11/828,267 filed Jul. 25, 2007 (U.S. Pat. Pub. No. 2008/0033290 A1); Ser. No. 12/118,439 filed May 9, 2008 (U.S. Pat. Pub. 2009/0030412 A1); Ser. No. 12/201,811 filed Aug. 29, 2008 (U.S. Pat. Pub. 2009/0062790 A1); and Ser. No. 12/209,057 filed Sep. 11, 2008 (U.S. Pat. Pub. 20090076498 A 1), may be utilized herewith. Each of these applications is incorporated herein by reference in its entirety.

In particular, such assemblies, apparatus, and methods may be utilized for treatment of various conditions, e.g., arrhythmias, through ablation under direct visualization. Details of examples for the treatment of arrhythmias under direct visualization which may be utilized with apparatus and methods described herein are described, for example, in U.S. patent application Ser. No. 11/775,819 filed Jul. 10, 2007 (U.S. Pat. Pub. No. 2008/0015569 A1), which is incorporated herein by reference in its entirety. Variations of the tissue imaging and manipulation apparatus may be configured to facilitate the application of bipolar energy delivery, such as radio-frequency (RF) ablation, to an underlying target tissue for treatment in a controlled manner while directly visualizing the tissue during the bipolar ablation process as well as confirming (visually and otherwise) appropriate treatment thereafter.

Steering of the hood assembly via controls on the handle may present some difficulties particularly when the catheter assembly has been contorted into various configurations by patient anatomies. This contortion may result in a mismatch between the steering controls and the corresponding movement on the screen of the in-vivo visualization system potentially leading to the user having to make constant micro movements on the steering controls to mentally re-map the direction of movement on the screen to the steering controls. This constant readjustment increases procedure times and may put undue stress and frustration on the user performing the treatment. This may continue to exist even with the addition of three-dimensional visualization systems as the movement of the catheter hood 12 may not correspond to the real-time images viewed on the screen projecting the tissue images. Directional indicators on the visualization screen, in-vivo visualization screen, as well as on the steering controls may help to give the user a sense of orientation of the catheter device with respect to the in-vivo image being viewed. With this sense of orientation, users of the catheter device may be intuitively aware of the direction in which they should manipulate the tip of the device in order to access a specific region of anatomy. Further details for use of directional indicators which may be utilized herein are shown and described in U.S. patent application Ser. No. 12/118,439 filed May 9, 2008 (U.S. Pat. Pub. No. 2009/0030412 A1), which is incorporated herein by reference in its entirety.

Figure 6:
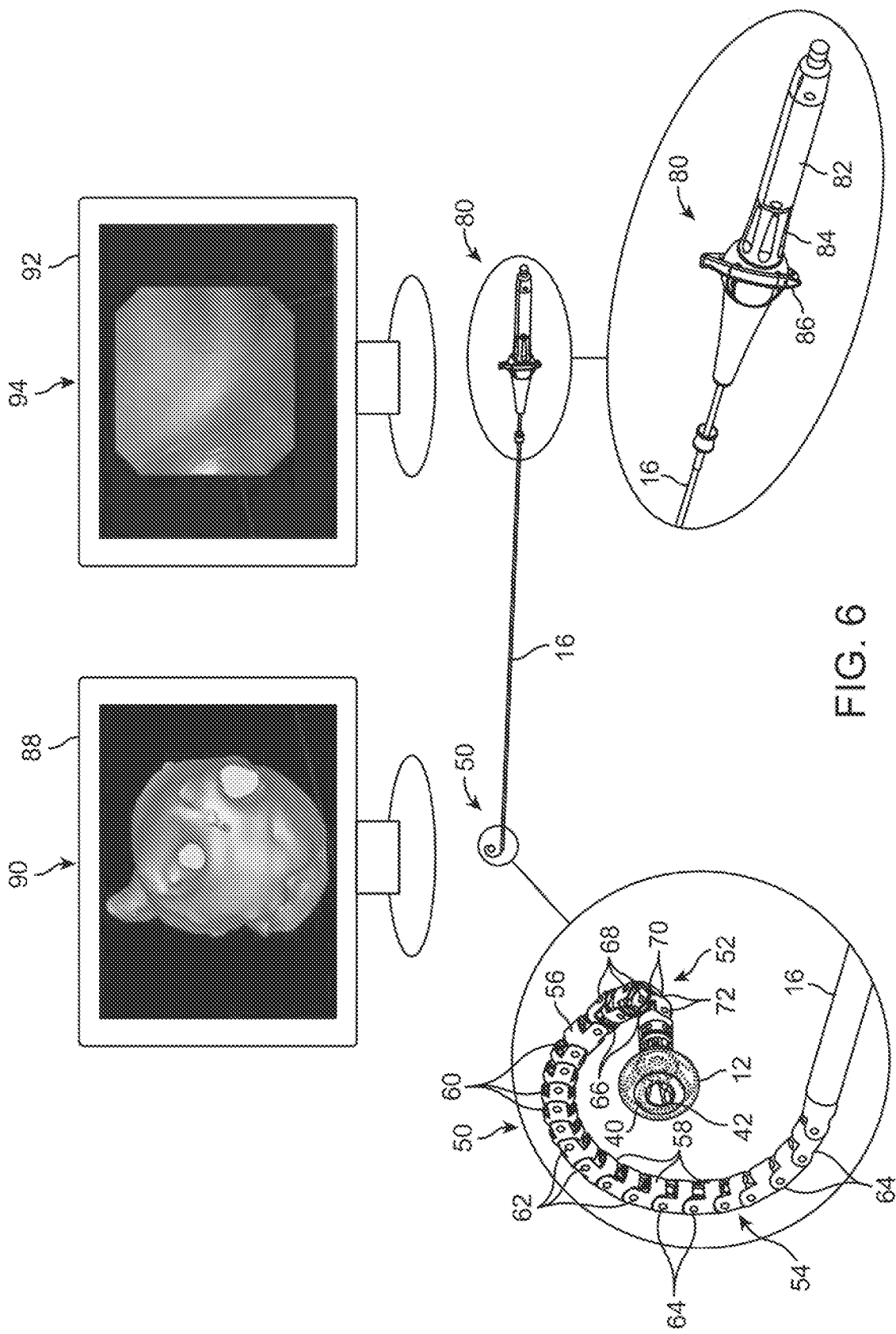
FIG. 6 shows one variation of an articulatable deployment catheter having a distal steerable section and a proximal steerable section with a three-dimensional model illustrating a representation of the hood assembly within the body and the visual image of the tissue region captured through the hood.

Turning now to the assembly view of FIG. 6, one variation of an articulatable deployment catheter 50 is shown which comprises a distal steerable section 52 and a proximal steerable section 54 located proximally of the distal steerable section 52. Further details of the deployment catheter 50 which may be used herein may be seen in further detail in U.S. patent application Ser. No. 12/108,812 filed Apr. 24, 2008 (U.S. Pat. Pub. No. 2008/0275300 A1) and U.S. patent application Ser. No. 12/618,306 filed Nov. 13, 2009, each of which is incorporated herein by reference in its entirety. As shown, the articulatable deployment catheter 50 may extend from the catheter 16 attached to handle assembly 80. In this variation, the handle assembly 80 may have a handle body 82 and an articulatable proximal steering control 84 which may be manipulated to steer a proximal steerable section 54 within a single plane of articulation. A separate distal steering control 86 which may be manipulated to steer a distal steerable section 52 in any of four planes or more independently of the proximal steerable section 54. A first monitor 88 may be in communication with the catheter assembly 50 to record and display a representative image of the hood 12 orientation of the device relative to the anatomy to show the positional information 90. A second monitor 92 may also be in communication with the catheter assembly 50 to display the visual images of the underlying tissue captured through the hood 12 to show the real-time visual images of tissue 94.

Additional control and navigation systems which may be utilized herein are shown and described in further detail in U.S. patent application Ser. No. 11/848,429 filed Aug. 31, 2007 (U.S. Pat. Pub. 2008/0097476 A1) and in Ser. No. 11/848,532 also filed Aug. 31, 2007 (U.S. Pat. Pub. 2009/0054803 A1), each of which is incorporated herein by reference in its entirety.

An intervening link 56 may couple the sections 52, to one another and provide a terminal link to which one or more pull wires may be attached in controlling one or both sections. The distal steerable section 52 may utilize individual links 66 which allow for the section 52 to be articulated in a variety of different directions and angles, e.g., four-way steering, to enable omni-direction articulation. The individual links 66 may accordingly utilize a body member 68 having a pair of yoke members 70 positioned opposite to one another and extending distally from the body member 68 and each defining an opening. A pair of pins 72 may each extend radially in opposing directions from body member 68 and in a perpendicular plane relative to a plane defined by the yoke members 70. The pins 72 of each link 66 may be pivotably received by the yoke members 70 of an adjacent link 66 such that the pins 72 and yoke members 70 are joined in an alternating manner. This alternating connection allows for the serially aligned links 66 to be articulated omni-directionally.

The links 58 of the proximal steering section 54 may also comprise a pair of yoke members 62 positioned opposite to one another and extending distally from body member 60. However, the pins 64 may extend radially in opposing directions while remaining in the same plane as that defined by yoke members 62. When joined together in series, each pin 64 of each link 58 may be pivotably received by the yoke members 62 of an adjacent link 58. Yet when joined, the composite proximal steering section 54 may be constrained to bend planarly within a single plane relative to the rest of the deployment catheter.

The combined distal steerable section 52 and a proximal steerable section 54 results in a proximal steering section which can be articulated in a single plane to retroflex the entire distal assembly and a distal steering section which can then be articulated any number of directions, e.g., four-way steering, to access anatomical structures within the heart or any other lumen. The assembly may thus be used, e.g., to create circumferential lesions around the ostia of the pulmonary veins in the left atrium while the underlying tissue remains under direct visualization through the hood.

In order to help physicians gain a better sense of the catheter hood orientation, color coded directional indicators, e.g., illustrated as dots or other symbols, may used to represent a specific section of the catheter hood 12. At least one of these color coded dots or symbols may be placed on a representation of the catheter assembly on the monitor, on the in vivo visualization monitor, and on the steering controls of the catheter handle. For illustrative purposes, the dots or symbols (which may also be optionally color-coded) may represent one of four directional indicators which may be represented on the monitors, as shown in FIG. 7A the representative image of a hood assembly is positioned within a generated three-dimensional model of the left atrial chamber LA of a heart in proximity to the pulmonary veins PV. The representative image of the hood assembly may be generated, as described previously, and imaged to show a real time representation of the hood orientation relative to the tissue.

The image of the positional information 100 may be seen where, e.g., a first directional indicator 102 shown as a blue dot, may be assigned a first position along the hood 12, a second directional indicator 104 shown as a red triangle, may be assigned a second position along the hood 12, a third directional indicator 106 shown as a yellow star may be assigned a third position along the hood 12, and a fourth directional indicator 108 shown as a green dot may be positioned along a fourth position along the hood 12. The dots or symbols are shown for illustrative purposes and they may represented by any number of symbols, letters, numbers, etc. so long as they represent indicators which are distinct from one another. Moreover, color-coding may be optionally incorporated and the number and positioning of the indicators may be varied so long as different directions may be discerned by the placement and number of indicators.

In addition to the generated representative orientation information shown in the displayed image 100, the captured images of the tissue which are visualized through the hood 12 and displayed, e.g., on a second monitor, may be seen in the visualized tissue image 94 of FIG. 7B. Each of the directional indicators 102, 104, 106, 108 may be seen along respective quadrants of the imaged tissue region. These directional indicators may be either imprinted on the distal membrane of the hood 12 such that they correspond with the directional indicators generated and displayed in image 100. Additionally or alternatively, these directional indicators may be generated by a processor and superimposed upon the images of the visualized tissue. Alternately, directional indicators may be placed on the surface of the second monitor 92 using colored stickers, translucent overlays or by marking with a pen on the surface of the monitor. Other variations may utilize directional indicators which may be shown as colored regions or bands 102', 104', 106', 108' which may be displayed and/or superimposed upon the imaged tissue, as shown in FIG. 7C. Further details are also shown and described in U.S. patent application Ser. No. 12/118,439 filed May 9, 2008, which is incorporated herein by reference in its entirety.

Figure 8A:
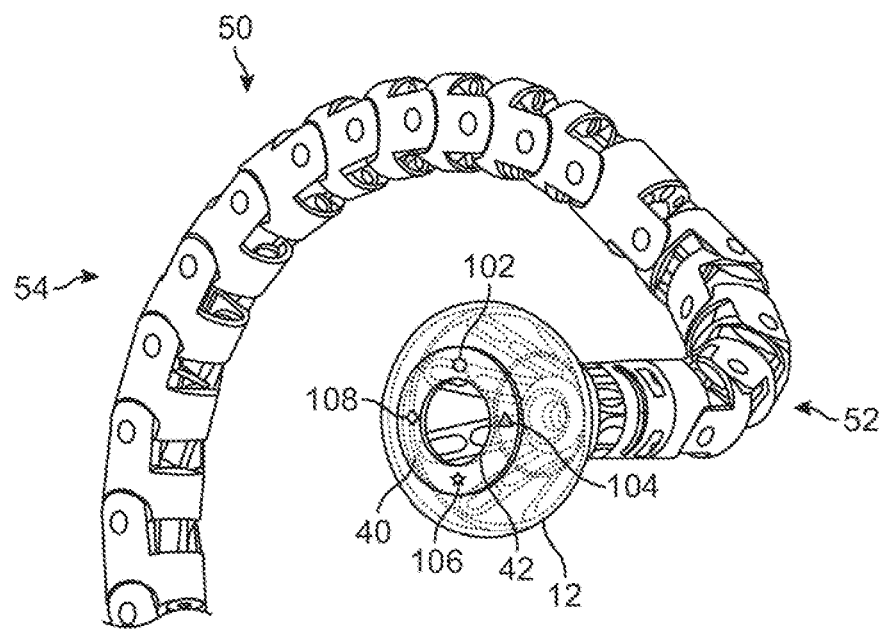
FIGS. 8A and 8B show perspective views of directional indicators positioned upon the hood as well as on the handle assembly which correspond with one another.
Figure 8B:
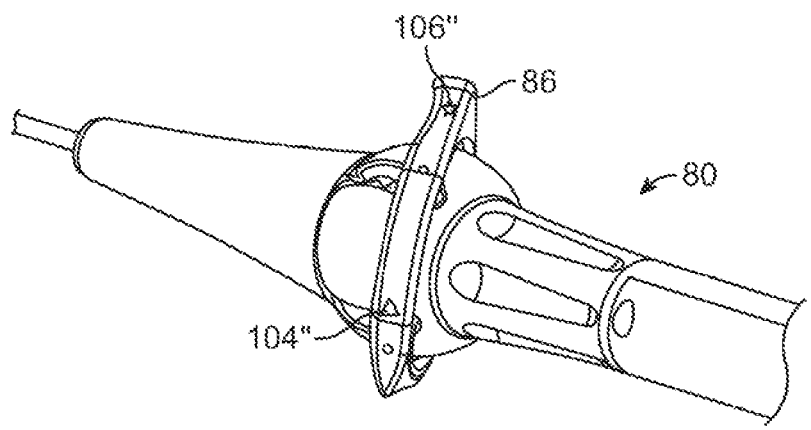

As previously mentioned and as seen in the perspective view of FIG. 8A, directional indicators 102, 104, 106, 108 may be imprinted directly upon the distal membrane 40 of the hood 12 in proximity to the aperture 42. Moreover, the handle assembly 80 may also define, e.g., the one or more markings 104", 106", etc., over the steering controls, as shown in the perspective view of FIG. 8B, which correspond with the identical or similar markings defined along the distal membrane 40 of hood 12. For example, the first directional indicator 102 at the first location along hood 12; the second directional indicator 104 at the second location along hood 12, the third directional indicator 106 at the third location along hood 12, and the fourth directional indicator 108 along the fourth location along hood 12 may be distinct from one another and may correspond to the indicators located on the control 86. Further details of catheter control handles which may be utilized herein are described in further detail in U.S. patent application Ser. No. 12/499,011 filed Jul. 7, 2009, which is incorporated herein by reference in its entirety.

As the user visualizes the tissue through hood 12, if the hood 12 needed to be repositioned in any particular direction along the tissue, the user may note the direction to be moved relative to the indicators marked on hood 12 and may thus manipulate the controls on control 86 accordingly such that movement of the controls in the chosen direction may articulate the hood 12 in the same direction. Additionally, the generated image of the hood orientation may also display the directional indicators corresponding to the indicators on the hood 12 and the handle 80. Such a feature may be highly advantageous relative to the absence of visual markings as it may be difficult for the user to steer the hood 12 in a desired direction after it is inserted into the patient's body due to the changes in hood orientation relative to the handle 80 orientation.

Figure 9A:
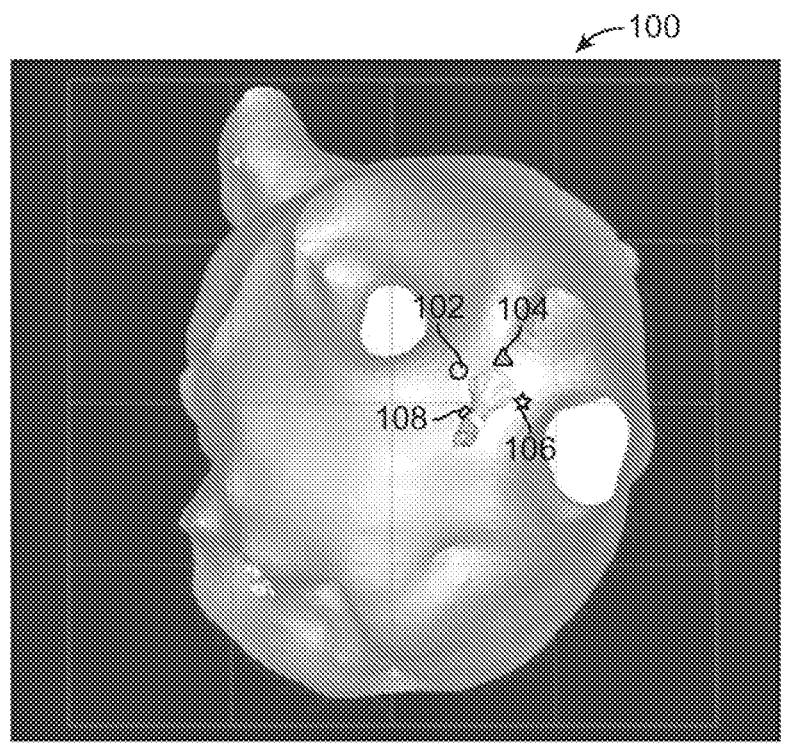
FIG. 9A shows a representative image of the hood assembly within a three-dimensional model of the left atrial chamber with the directional indicators imaged thereon.
Figure 9B:
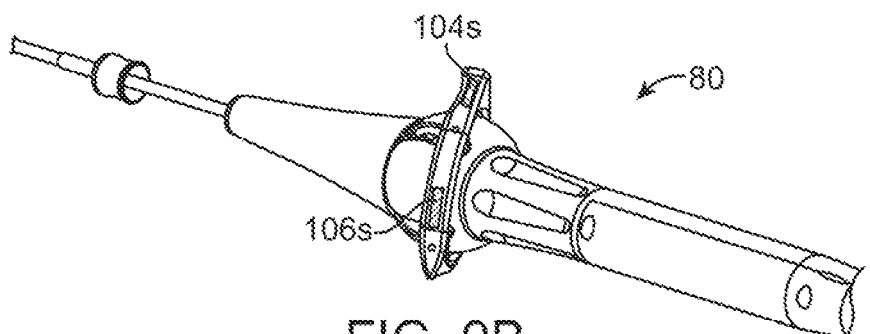
FIGS. 9B and 9C show perspective views of a handle assembly having touch-sensitive sensors on the manipulation control.
Figure 9C:
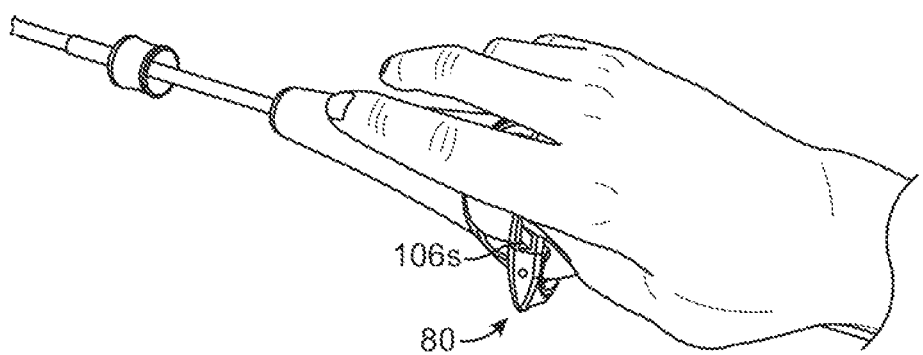

In yet another variation, one or more of the directional indicators located on the handle assembly 80 may be configured as tactile sensors. An example is shown in the perspective view of FIG. 9B which shows the directional indicators, which may be color-coded, configured as touch-sensitive sensors 104s, 106s, etc. When a user places their hand or finger upon one of the tactile sensors, such as sensor 106s as shown in FIG. 9C, the corresponding directional indicator 106 displayed on positional image 100 in FIG. 9A may begin to blink, flash, or otherwise provide some indication that the corresponding direction on the control handle 80 has been activated thus giving the user an immediate indication as to which portion of the handle control to manipulate without having to move their eyes from the monitors. In addition, when a user places their hand or finger upon one of the tactile sensors, such as sensor 106s as shown in FIG. 9C, the corresponding directional indicator 106' displayed on the tissue image 94 in FIG. 7B may begin to blink, flash, or otherwise provide some indication that the corresponding direction on the control handle 80 has been activated thus giving the user an immediate indication as to which portion of the handle control to manipulate without having to move their eyes from the monitors. The touch-sensitive sensors located on the handle assembly 80 may be configured as touch-sensitive sensors utilizing any number of known mechanisms, such as capacitive sensors or pressure-sensitive sensors, etc.

Aside from the use of directional indicators and generated positional information, other mechanisms may be utilized for making the manipulation and steering of the hood relative to the body more intuitive. One example may utilize rotation of the image on the monitor showing the visualized tissue to affix a direction on the monitor to a direction of mechanical actuation on the control handle depending upon how the handle is re-orientated. For example, as shown in the perspective view of FIG. 10A, the control 86 on handle assembly 80 may be articulated in a first direction 114 by manipulating the control 86 along the directional indicator 106s. This may result in the hood 12 moving in a first direction such that the imaged tissue 110 through the hood 12, as shown in FIG. 10B, accordingly moves to the left relative to the tissue, as shown in the imaged tissue 112, as shown in FIG. 10C.

Figure 11A:
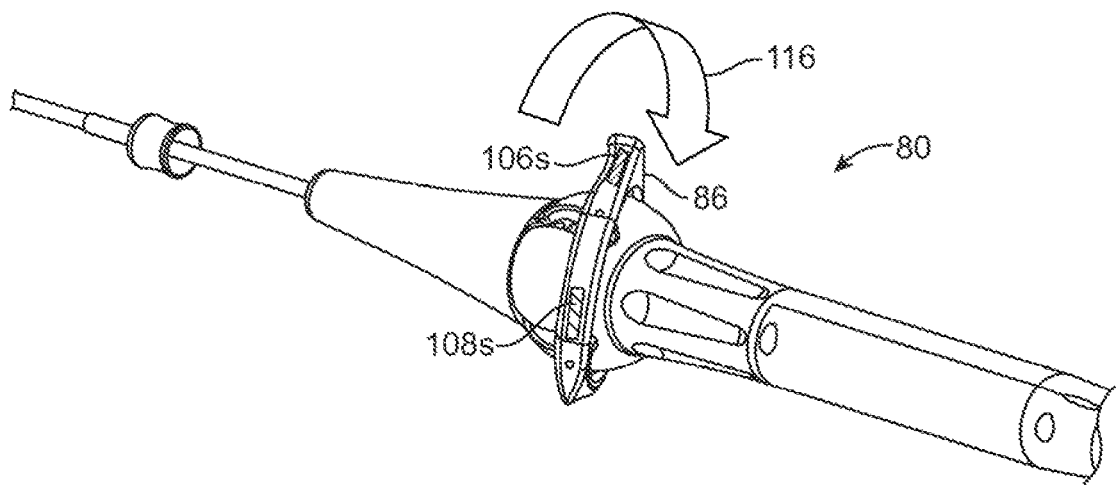
FIGS. 11A to 11C show the handle assembly of FIG. 10A rotated about its longitudinal axis and manipulated again in the first direction to move an imaged region in a consistent manner, respectively.
Figure 11B:
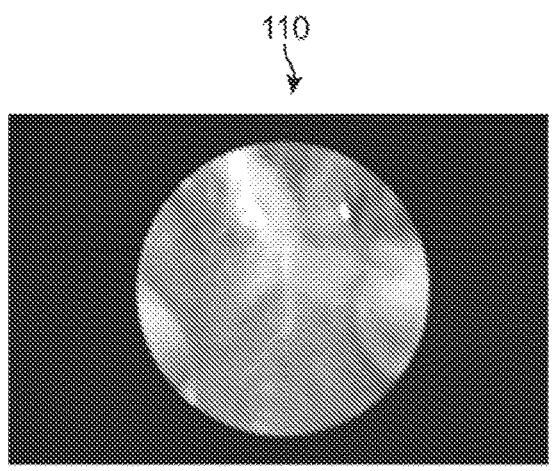
Figure 11C:
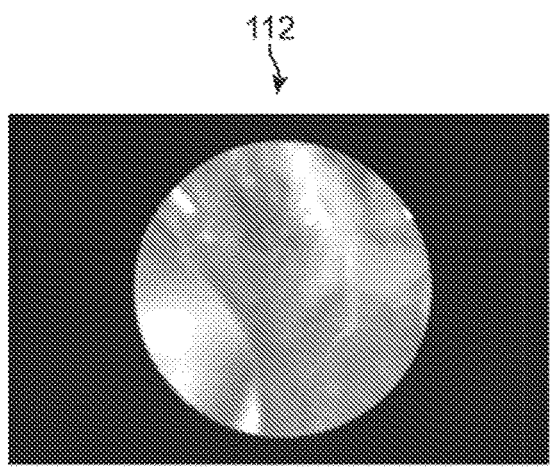

Because of the tortuous nature of patient anatomies, the handle assembly 80 may be rotated about its longitudinal axis relative to the user to position the hood at the distal end of the catheter assembly within the body. As shown in the perspective view of FIG. 11A, handle assembly 80 is shown rotated about its longitudinal axis in a direction or rotation 116. The directional indicator 106s may be seen as rotated, e.g., 90 degrees away, into a different position relative to the user such that the directional indicator 108s now is proximate to the user. Actuation of the control 86 along the directional indicator 108s may again result in a movement of the hood 12 to the left, as shown by the imaged tissue 110 being moved to the left as shown by the imaged tissue 112. In this manner, regardless of the rotation of the catheter handle 80 actuation of the control 86 may result in consistent movement of the hood, i.e., actuation to the left results in movement of the hood 12 to the left, actuation to the right results in movement of the hood 12 to the right, etc.

Such movement may be achieved by mechanical mechanisms, such as having a portion of the catheter handle 80 being rotatable about its longitudinal axis to maintain a consistent position of the handle relative to the user. Examples of such a catheter handle assembly as shown and described in further detail in U.S. Prov. App. 61/286,283 filed Dec. 14, 2009 and 61/297,462 filed Jan. 22, 2010, each of which is incorporated herein by reference in its entirety. Alternatively, one or more accelerometers or positional sensors may be incorporated into the handle assembly 80 which communicate with a processor such that movement of the handle assembly 80 from an initial calibrated position may automatically rotate the images on the monitor to align in a corresponding manner with the rotation of the handle assembly 80.

Figure 12A:
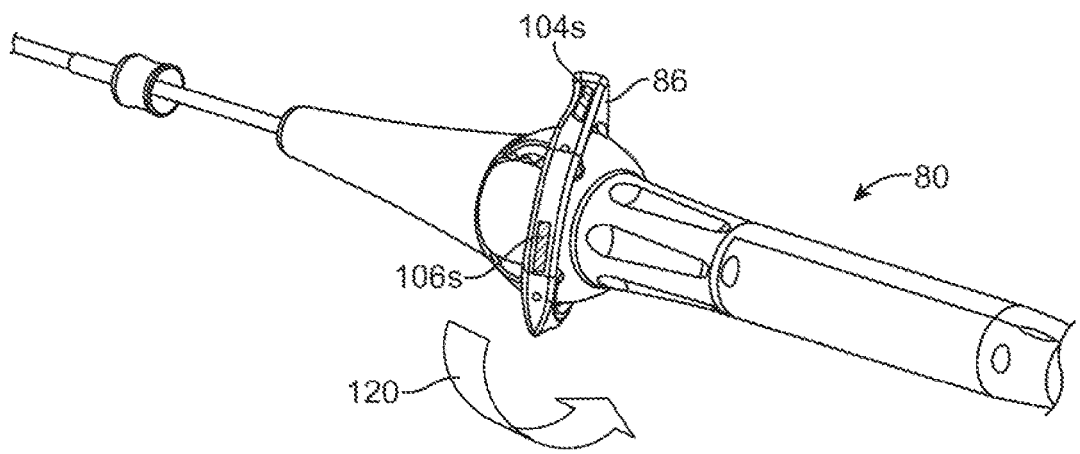
FIGS. 12A to 12C show another example of a perspective view of a handle assembly manipulated in a first direction to move an imaged region, respectively.
Figure 12B:
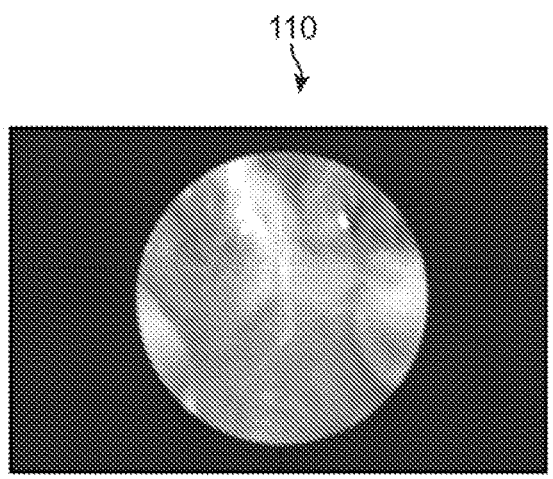
Figure 12C:
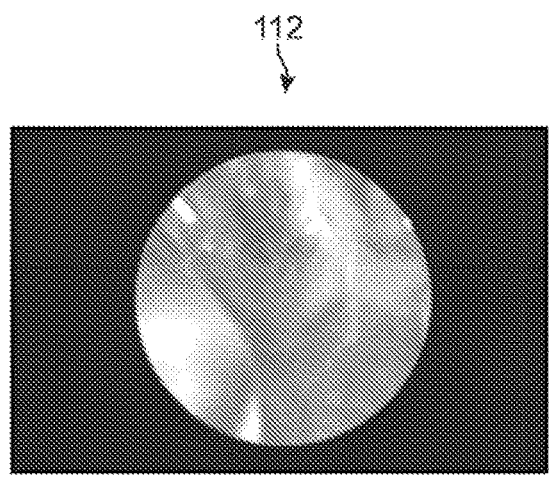
Figure 13A:
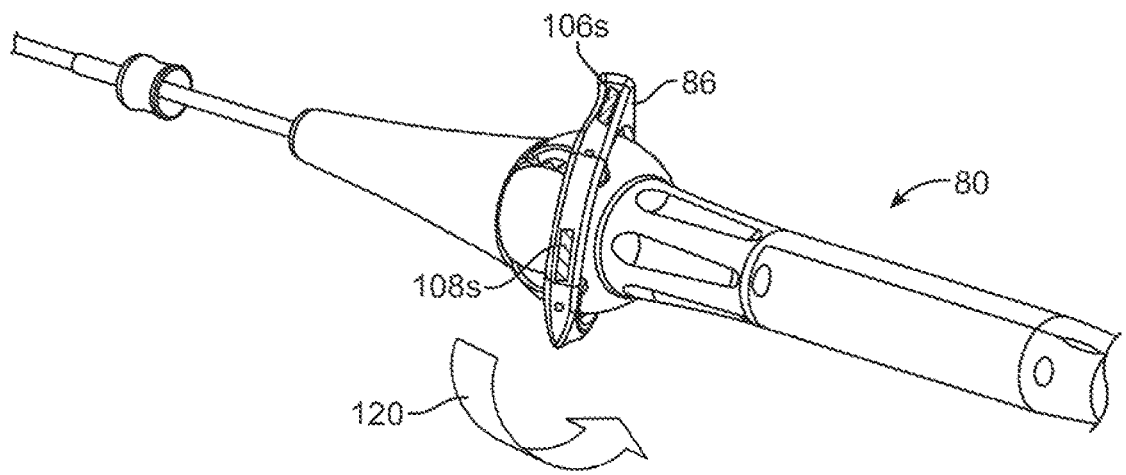
FIGS. 13A to 13C show the handle assembly of FIG. 12A rotated about its longitudinal axis and manipulated again in the first direction to move an imaged region in a consistent manner, respectively.
Figure 13B:
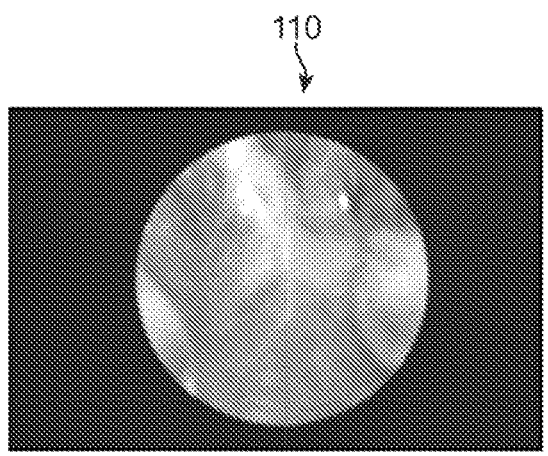
Figure 13C:
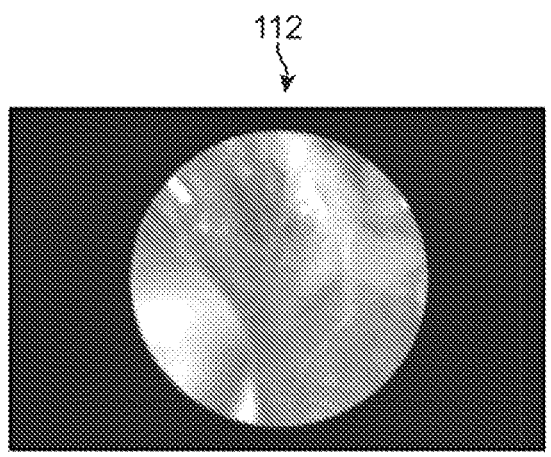

In another variation, rather than rotating the images of the tissue based on the movement and rotation of the catheter handle, the images of the tissue may be fixed and the steering controls instead may be remapped. An example is shown in the perspective view of FIG. 12A which shows catheter handle 80 manipulated along a first direction 120 by manipulating control 86 along directional indicator 106s. The resulting imaged tissue 110, shown in FIG. 12B, may be accordingly moved in a first corresponding direction, e.g., to the left as shown in the moved tissue image of FIG. 12C. As the handle assembly 80 is rotated to accommodate positioning of the hood within the body, as shown in FIG. 13A, the previously-articulated directional indicator 106s may be seen rotated into a new position relative to a user. Manipulation of the control 86 along the same direction 120 as previously performed but this time along directional indicator 108s may nonetheless result in the imaged tissue 110, as shown in FIG. 13B, being moved again in the same direction as shown in the imaged tissue 112 of FIG. 13C. In this example, the steering controls are constantly remapped such that tissue image as seen on the monitors always move in a direction that corresponds to the spatial orientation of the steering control 80. This may be accomplished by utilizing, e.g., electronically-actuated mechanisms within handle assembly 80 which are controlled via a processor in communication with one or more accelerometers or position sensors. Such a system may automatically map and re-map the control 86 with the electronically-actuated mechanisms depending upon the orientation of the handle assembly 80 relative to an initially calibrated orientation.

Figure 14A:
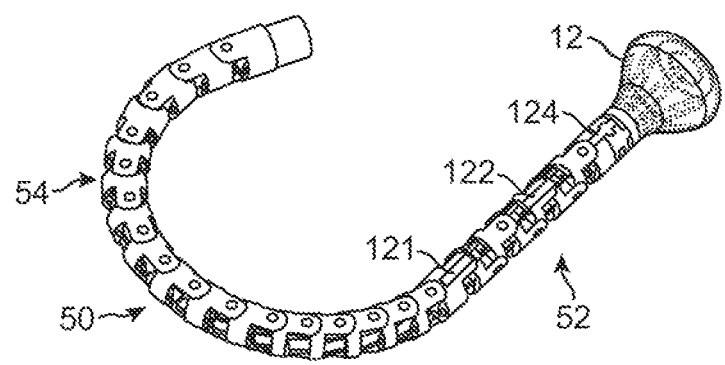
FIG. 14A shows a perspective view of a hood assembly having one or more sensors positioned along at least one of the steerable sections.
Figure 14B:
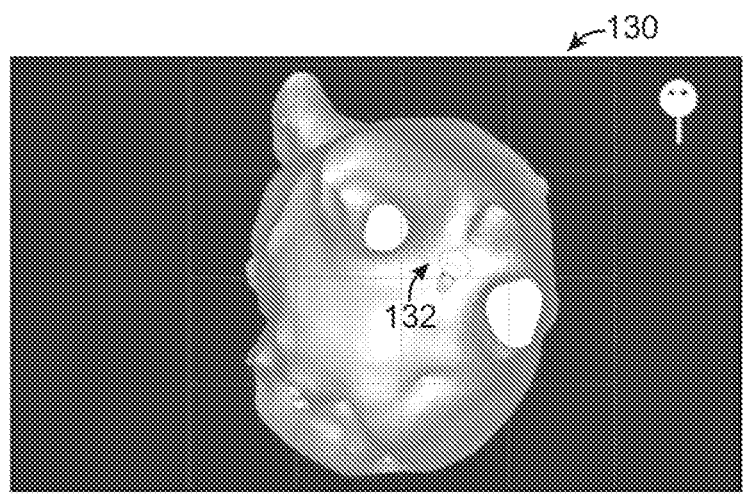
FIGS. 14B and 14C show three-dimensional generated models illustrating representative images of the hood assembly and its curved steerable segment relative to the tissue.
Figure 14C:
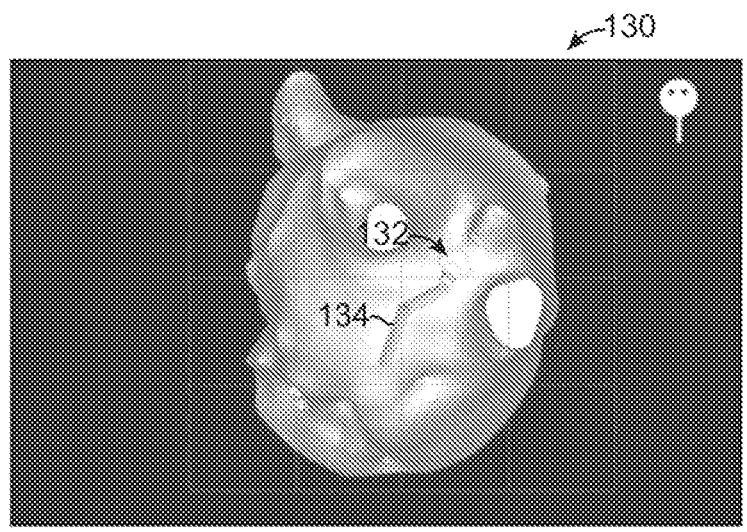

In generating a representative image of the hood assembly orientation relative to the tissue surface, one or more sensors may be positioned along the catheter device for generating the images, as previously described, e.g., in U.S. patent application Ser. No. 11/848,532 filed Aug. 31, 2007 (U.S. Pat. Pub. 2009/0054803 A1), which has been previously incorporated herein by reference above. Additional sensors may be placed along the steerable sections of the catheter assembly such that an image of the relative positioning of the catheter and hood assembly may be generated for graphical representation. As shown in the perspective view of FIG. 14A, multiple sensors 121, 122, 124 may be positioned at intervals along the distal steerable section 52. Additional sensors may also be positioned optionally along the proximal steerable section 54 as well. The resulting generated image 130 of the hood assembly 132 may be seen in FIG. 14B and the representative hood assembly 132 as well as the representative distal steerable section 134 may also be seen in the image of FIG. 14C. Providing the representative image of one or both steerable sections may provide the user the ability to observe the complex curve of the steerable sections for discerning if the catheter is at its contortion limit as the hood assembly is in proximity of the target tissue to allow for a faster and more intuitive movement of the catheter from one tissue region to another region without reaching contortion limits or over-steering the catheter assembly.

Figure 15A:
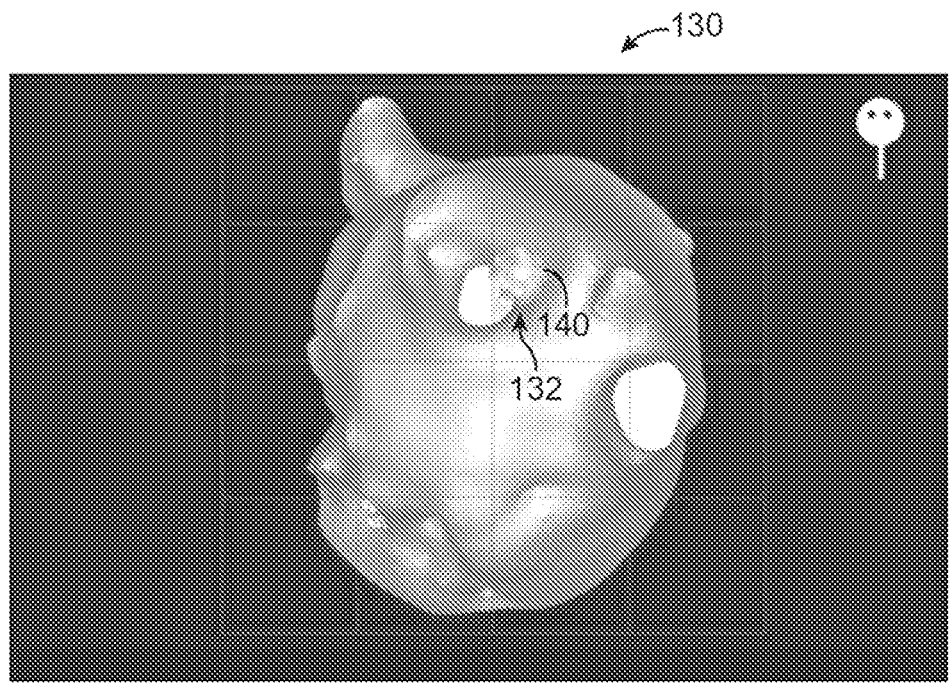
FIG. 15A shows an example of a three-dimensional generated model illustrating a representative image of the hood assembly and an image of tissue captured from the hood and superimposed upon the model.

In yet another variation for facilitating tissue treatment, the captured visual image of the tissue as imaged through the hood 12 may be projected and mapped to the representative map of the tissue anatomy. Being able to visualize the "active spot" 140 that is being visualized through the hood, shown by its representation 132, by mapping it onto the surface of the representative three-dimensional model 130 may allow the physician to more accurately navigate the anatomy, as shown in FIG. 15A. When visualizing and treating tissue using the visualization system, the catheter hood may not necessarily be visualizing the tissue that is seen on the in vivo visualization system. This may occur due to a variety of reasons such as non-perpendicularity of the hood to the tissue surface or contortion of the hood. Because the active spot moves as the catheter hood is being moved, this may give the physician a greater awareness and confidence on both the visualization systems.

The three-dimensional model 130 may be normally created by a sensor probe which is pushed against the walls of the anatomy. The associated data points are taken and a representative model is built. Often the model is inaccurate and physicians rely on approximations to make decisions on locations for tissue treatment. Cross-referencing the data points of the three-dimensional model with images viewed by the in vivo visualization system can be helpful in making adjustments and adding further detail to the model. Visual features such as pulmonary vein ostia could potentially be referenced to the three-dimensional model by location and contour matching software algorithms in addition to manual point selection.

Figure 15B:
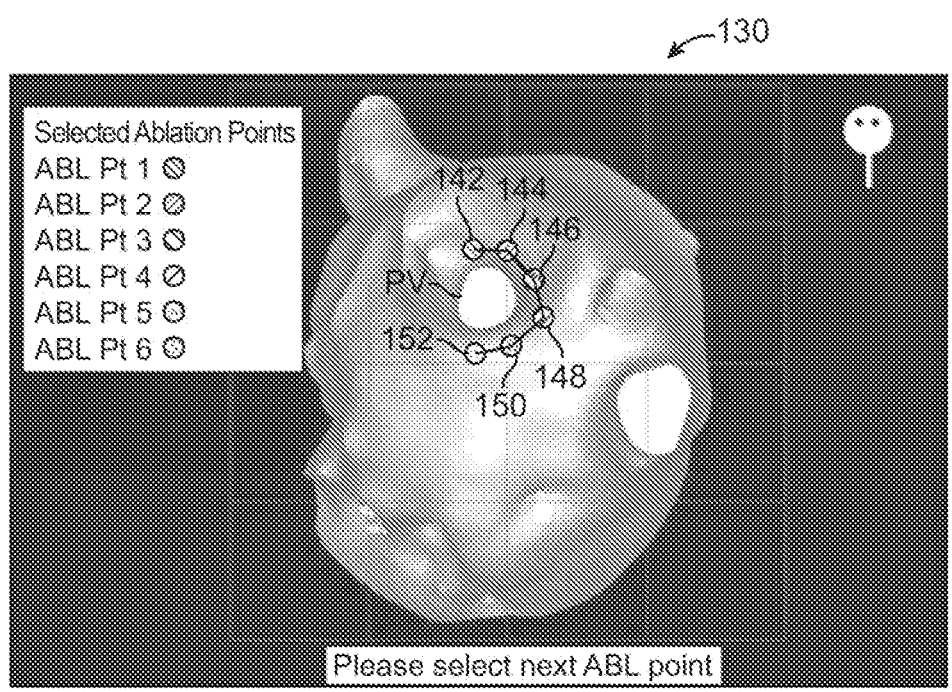
FIG. 15B shows another example of a three-dimensional generated model illustrating pre-selected way points for ablation treatment imaged upon the model.
Figure 16A:
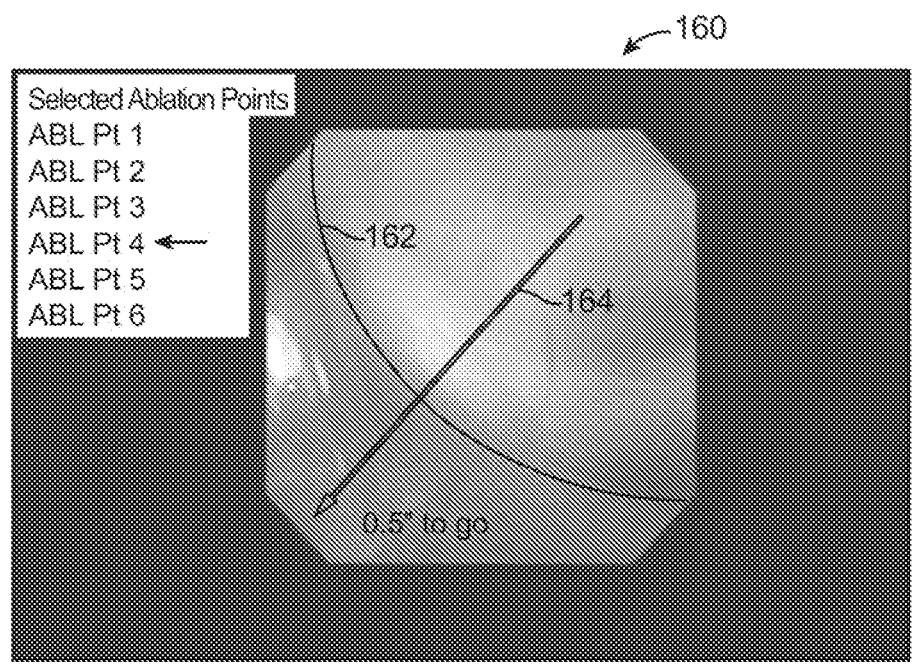
FIG. 16A shows an imaged region of tissue visualized through the hood with navigational information superimposed upon the image.

In yet another example, way-pointing methods may also be utilized to facilitate tissue treatment by the physician. Way-pointing is a pre-operative method that allows the physician to map out the ablation procedure by selecting lesion sites on the three-dimensional model of the anatomy. As shown in the image model 130 of FIG. 15B, one or more lesion sites, e.g., 142 to 152, at least partially around the pulmonary vein PV ostium, may be pre-selected on the three-dimensional model 130. This data may be then transmitted to the catheter system which may generate and project approximated lesion boundaries 162 to be formed as well as the navigational information 164 to guide the hood from one lesion to another as the procedure progresses, as shown in the direct visual image 160 captured through the hood 12 and projected on a monitor with the way-pointing and navigational information superimposed on the tissue image, as shown in FIG. 16A. Such a way-pointing system may prevent the user from becoming disoriented in the anatomy of the heart and may effectively speed procedure times while ensuring that lesions are contiguously formed, if necessary or desired, by showing lesion boundaries.

Figure 16B:
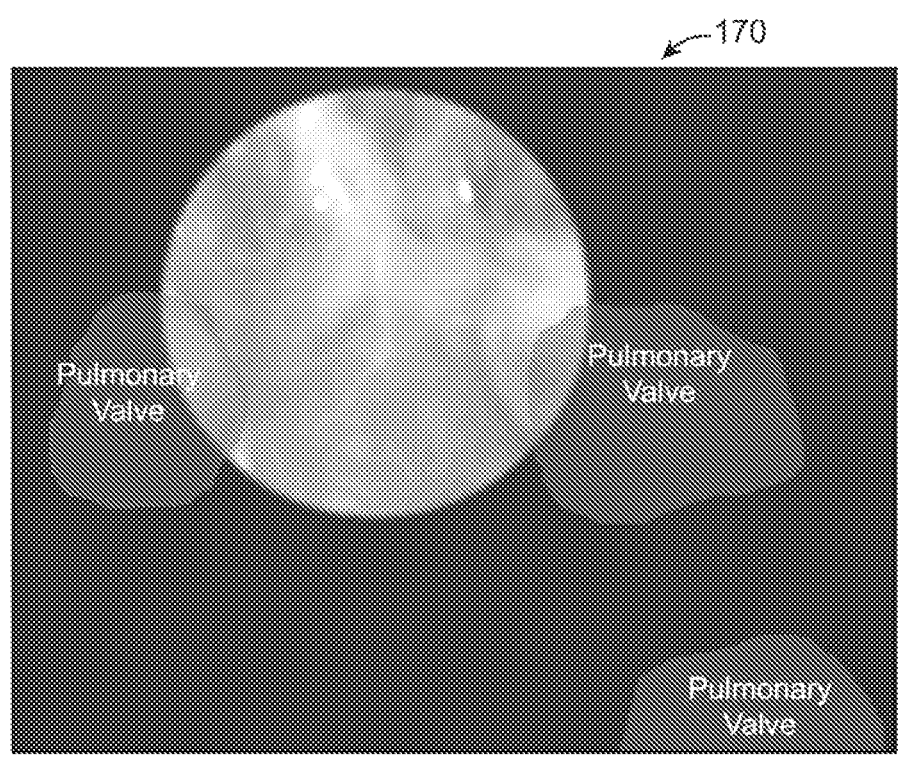
FIG. 16B shows another example of an imaged region of tissue visualized through the hood with anatomical in proximity to the imaged region superimposed upon the tissue image.

Additionally and/or alternatively, other methods for helping the user to maintain spatial awareness of the surrounding tissue and anatomical features may also be utilized for facilitating navigation, safety, procedure efficacy, etc. FIG. 16B shows an example of an imaged tissue region 170 with indicators of areas of interest beyond the field of view of the catheter hood. As an illustration, the pulmonary vein locations have been indicated in the figure but points of interest may also include unique anatomical features, locations of probes such as a probe positioned in the esophagus, location of the lung, patent foramen ovale, and among other things. The features to be displayed may be pre-selected on the three-dimensional visualization model prior to treatment. These points of interest may allow the user to establish a base of reference when they are viewing the images of tissue on the monitor. Additionally, the indication of surrounding tissue regions may help to ensure the avoidance of inadvertently treating tissue treatment surrounding the tissue region of interest.

Figure 17:
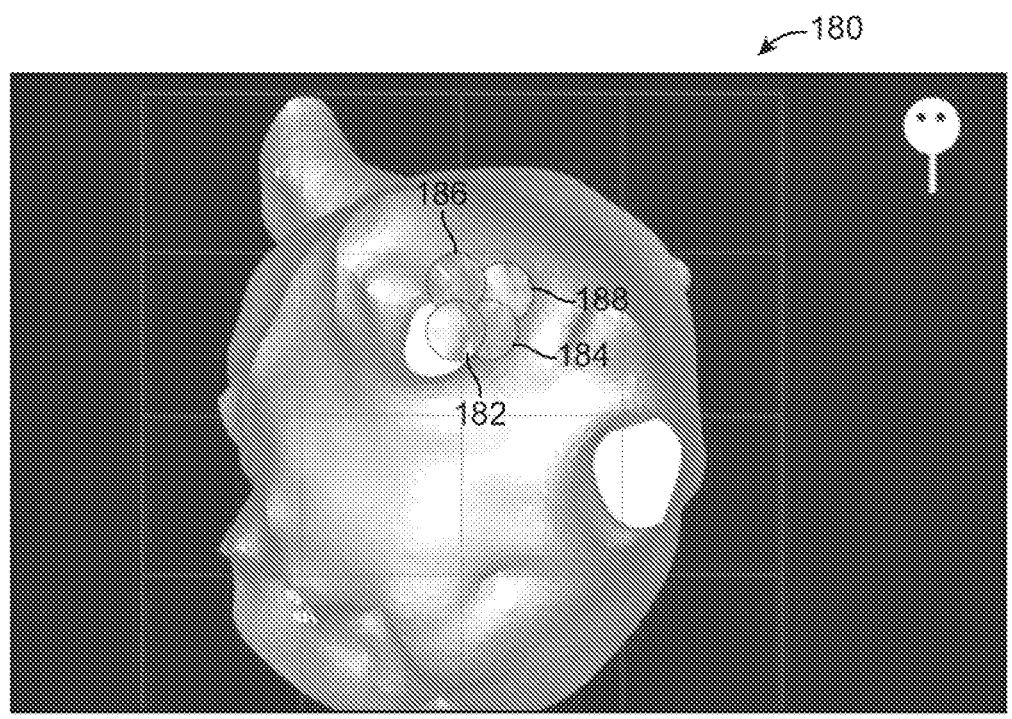
FIG. 17 shows another example of a three-dimensional generated model having multiple tissue images stitched together and superimposed upon the model.

Yet another example for facilitating tissue treatment procedures may utilize the augmentation of images utilizing previously captured images. For instance, as shown in the three-dimensional model 180 of FIG. 17, captured images 182, 184, 186, 188 previously visualized through the hood and recorded may be compiled and stitched relative to one another to provide a seamless interior map of the anatomy. This image stitching may present an actual map of the interior of the heart instead of an approximate three-dimensional model. Moreover, the images can also be mapped such that they take on the contours of the model. Being able to see the actual visual inside the heart may increase physician confidence and also the speed of the procedure. Further examples and details are shown and described in U.S. patent application Ser. No. 11/848,532 filed Aug. 31, 2007 (U.S. Pat. Pub. 2009/0054803 A1), which has been previously incorporated herein above.

Figure 18A:
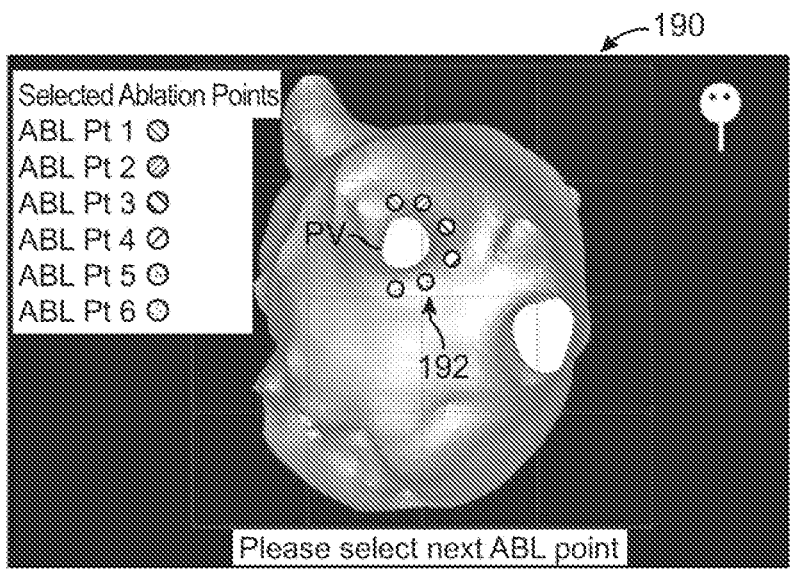
FIGS. 18A to 18C show another example of a three-dimensional generated model having pre-selected ablation points and representative images of the hood assembly idealized for treatment along these ablation points.
Figure 18B:
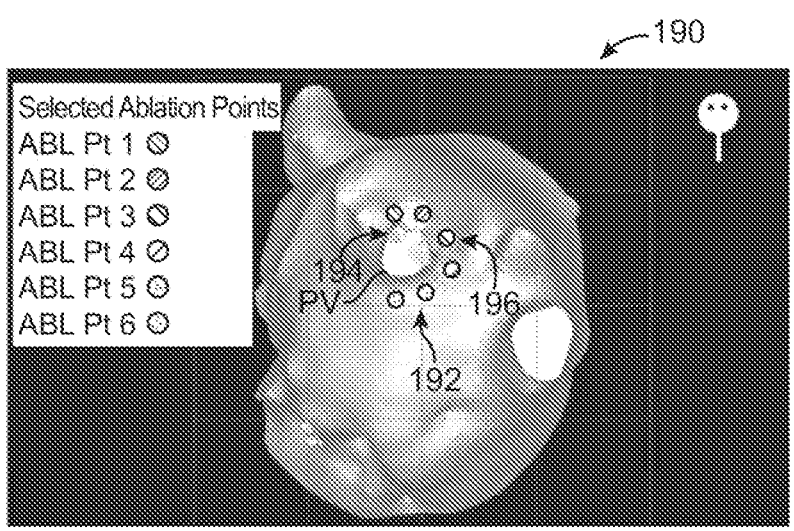
Figure 18C:
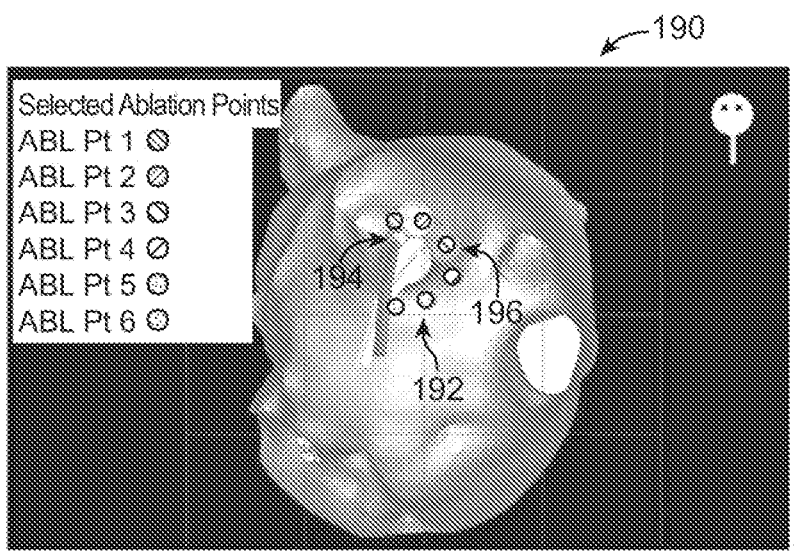

Procedure guidance systems are particularly useful when the user may be unfamiliar with the device and its capabilities or wish to facilitate the procedure by minimizing steering decisions from one ablation point to another. Such a system may function by first allowing the user to select potential ablation sites 192, e.g., in proximity to a pulmonary vein PV ostium, on either a pre-operative three-dimensional model or on a uniquely generated three-dimensional model 190 as shown in FIG. 18A. FIG. 18B shows various idealized positions and orientations of the representation of the hood 194, 196 in order to create optimal lesions taking into account the anatomical contours and structure. Physicians can then navigate the catheter hood into the particular orientation before performing ablation. Additionally, for steerable sections with a plurality of sensors, the steerable section can be graphically represented as well, as previously described. FIG. 18C is an illustrative example of such a system in which the hood assembly 194 indicates the current position and the idealized hood assembly 196 represents the idealized position and orientation of the hood and the steerable section in order to perform the next ablation optimally.

Figure 19:
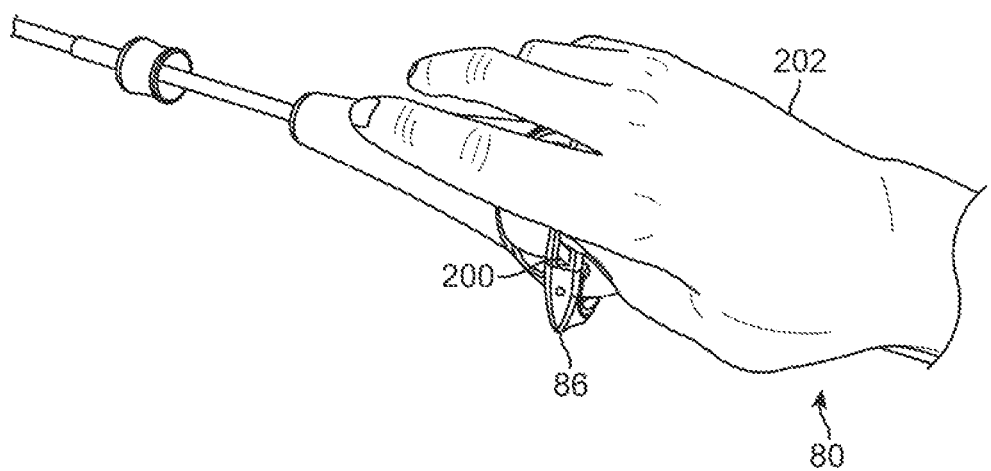
FIG. 19 shows a perspective view of a handle assembly variation configured to generate tactile sensations such as force feedback on the steering control for providing force feedback to the user's hand.

FIG. 19 also shows a variation in which the handle assembly 80 may generate tactile sensations such as force feedback on the steering control 200 for providing force feedback to the user's hand 202 so that the user is prompted to steer the catheter into the most optimal and efficient manner to move from one location to another. Such a tactile sensation feature may be utilized with any of the variations described herein.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A computer implemented method comprising:
   receiving a model of a tissue region;
   steering a distal end of a catheter within a body to a first area of a tissue region;
   obtaining a first image from the distal end of the catheter of the first area of the tissue region;
   mapping the first image of the first area of the tissue region to the model of the tissue region;
   displaying the first image of the first area of the tissue region on the model of the tissue region by superimposing the first image onto a surface of the model while the distal end of the catheter is at the first area;
   obtaining a second image from the distal end of the catheter of a second area of the tissue region;
   mapping the second image of the second area of the tissue region to the model of the tissue region; and
   displaying the second image of the second area of the tissue region on the model of the tissue region by superimposing the second image onto the surface of the model while the distal end of the catheter is at the second area.

2. The computer implemented method of claim 1 wherein the model is three-dimensional.

3. The computer implemented method of claim 1 further comprising
   steering the distal end of the catheter from the first area to the second area of the tissue region.

4. The computer implemented method of claim 1 further comprising projecting a graphic representation of the distal end of the catheter on the model of the tissue region.

5. The computer implemented method of claim 1 wherein obtaining the first image includes obtaining the first image through an open area created by an expanded hood extending from the distal end of the catheter.

6. The computer implemented method of claim 5 wherein obtaining the first image includes obtaining the image through a purging fluid occupying the open area created by the expanded hood.

7. The computer implemented method of claim 1 wherein steering includes activating a control mechanism coupled to a proximal end of the catheter.

8. The computer implemented method of claim 1 wherein receiving the model includes receiving a pre-operative model of the tissue region.

9. The computer implemented method of claim 1 wherein receiving the model includes generating the model from sensor data referencing position information in the tissue region.

10. The computer implemented method of claim 1 wherein receiving the model includes generating the model from a plurality of captured images.

11. The computer implemented method of claim 1 further comprising displaying an image of the distal end of the catheter on the model of the tissue region.

12. The computer implemented method of claim 1 further comprising receiving sensor data from a sensor positioned along a steerable section of the catheter.

13. The computer implemented method of claim 12 further comprising generating an image of the steerable section of the catheter for display on the model of the tissue region.

14. The computer implemented method of claim 1 further comprising adjusting the model based on information from the first image.

15. The computer implemented method of claim 1 wherein obtaining the first image includes obtaining image data from an imaging element at the distal end of the catheter.

16. The computer implemented method of claim 1 wherein the first area of the tissue region is distal of the distal end of the catheter.

17. The computer implemented method of claim 1 wherein mapping the first image to the model comprises matching a location of an anatomic feature visible in the first image with a location of the anatomic feature on the model.

18. The computer implemented method of claim 1 wherein mapping the first image to the model comprises matching a contour visible in the first image with the model.

19. The computer implemented method of claim 1 wherein mapping the first image to the model comprises referencing a plurality of data points of the model to the first image.

20. The computer implemented method of claim 1 further comprising:
   selecting sites of interest on the model of the tissue region;
   based on the selected sites of interest, generating site boundaries or navigational information; and
   displaying the site boundaries or the navigational information on the model of the tissue region.

* * * * *